(12) United States Patent
Boechat et al.

(10) Patent No.: US 10,538,515 B2
(45) Date of Patent: Jan. 21, 2020

(54) ISATIN-DERIVED COMPOUNDS, USE OF THE COMPOUNDS FOR THE TREATMENT OF AIDS AND METHOD OF TREATMENT USING THESE COMPOUNDS

(71) Applicant: FUNDAÇÃO OSWALDO CRUZ, Rio de Janeiro (BR)

(72) Inventors: Nubia Boechat, Rio de Janeiro (BR); Mônica Macedo Bastos, Rio de Janeiro (BR); Thiago Moreno Lopes E Souza, Rio de Janeiro (BR); Débora Inácio Leite, Rio de Janeiro (BR); Alice Maria Rolim Bernardino, Rio de Janeiro (BR)

(73) Assignee: FUNDAÇÃO OSWALDO CRUZ, Rio de Janeiro (BR)

( * ) Notice: Subject to any disclaimer, the term of this patent is extended or adjusted under 35 U.S.C. 154(b) by 0 days.

(21) Appl. No.: 16/099,901

(22) PCT Filed: May 10, 2016

(86) PCT No.: PCT/BR2016/000050
§ 371 (c)(1),
(2) Date: Nov. 8, 2018

(87) PCT Pub. No.: WO2017/193180
PCT Pub. Date: Nov. 16, 2017

(65) Prior Publication Data
US 2019/0177305 A1    Jun. 13, 2019

(51) Int. Cl.
C07D 405/14     (2006.01)
A61P 31/18      (2006.01)
C07F 9/6558     (2006.01)

(52) U.S. Cl.
CPC ............ *C07D 405/14* (2013.01); *A61P 31/18* (2018.01); *C07F 9/65583* (2013.01)

(58) Field of Classification Search
None
See application file for complete search history.

(56) References Cited

PUBLICATIONS

Boechat et al. "Design, Synthesis and Pharmacological Evaluation of HIV-1 Reverse Transcriptase Inhibition of New Indolin-2-Ones", Medicinal Chemistry, 2007, 3, pp. 533-542.
Costa et al. "0 Efavirenz: Relação Estrutura-Atividade e Métodos de Síntese", Rev. Virtual Quim., 2015, vol. 7, No. 4, pp. 1347-1370.
International Search Report and Written Opinion dated Aug. 25, 2016 issued in International Application No. PCT/BR2016/000050.
Medvedev et al. "Biological targets for isatin and its analogues: Implications for therapy", Biologics:Targets & Therapy 2007:1(2), pp. 151-162.
Palasz et al. "In search of uracil derivatives as bioactive agents. Uracils and fused uracils: Synthesis, biological activity and applications", European Journal of Medicinal Chemistry 97 (2015) pp. 582-611.
Pawar et al. "Design, docking study and ADME prediction of Isatin derivatives as anti-HIV agents", Med Chem Res (2011) 20:370-380.
Rane et al. "A Recent Perspective on Discovery and Development of Diverse Therapeutic Agents Inspired from Isatin Alkaloids", Current Topics in Medicinal Chemistry, 2016, 16, pp. 1262-1289.
Sirivolu et al. "Clicking 3'-azidothymidine into Novel Potent Inhibitors of Human Immunodeficiency Virus", J. Med. Chem. Nov. 14, 2013; 56(21): pp. 8765-8780.

*Primary Examiner* — Alicia L Otton
(74) *Attorney, Agent, or Firm* — Arent Fox LLP

(57) ABSTRACT

This invention relates to HIV-inhibiting compounds consisting of other Formulae I, II or III isatin derivatives, as shown below (Formulae I, II and III), whereby in Formulae I, II and III, $R_1$ is selected from H, $CH_3$ or Cl; $R_2$ is selected from one of the following radicals: zidovudine, amprenavir or an acyclic phosphonate chain, as shown below. This invention also relates to the use and treatment method using the Formulae I, II and III compounds. According to this invention, these compounds are also used for the treatment of infections caused by HBV or co-infection caused by HIV and HBV.

10 Claims, No Drawings

ISATIN-DERIVED COMPOUNDS, USE OF THE COMPOUNDS FOR THE TREATMENT OF AIDS AND METHOD OF TREATMENT USING THESE COMPOUNDS

CROSS-REFERENCE TO RELATED APPLICATION

This application is a 35 U.S.C. § 371 National Phase of PCT Application No. PCT/BR2016/000050 filed May 10, 2016, the disclosure of which is hereby incorporated by reference herein.

FIELD OF THE INVENTION

Acquired Immunodeficiency Syndrome (AIDS) is an infectious and contagious disease caused by the Human Immunodeficiency Virus (HIV). Antiretroviral drugs are used for the treatment of AIDS, as well as their combinations. However, ongoing treatment with these drugs led to the development of resistance mechanisms, requiring research in order to find new therapeutic options for the treatment of this disease.

Consequently, this invention relates to HIV-inhibiting compounds that consist of Formulae I, II or III isatin derivatives, as shown below:

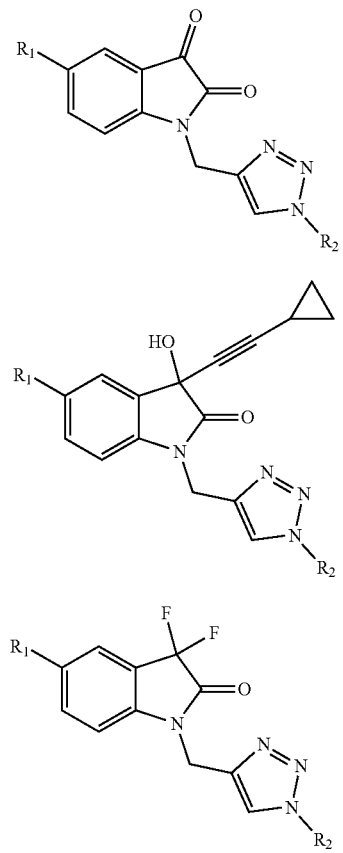

whereby in Formulae I, II and III:
$R_1$ is selected from H, $CH_3$ or Cl
$R_2$ is selected from one of the following radicals: zidovudine, amprenavir or an acyclic phosphonate chain, as shown below:

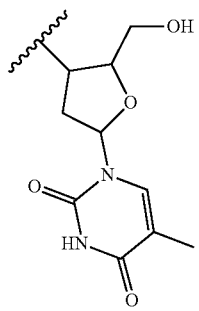

zidovudine

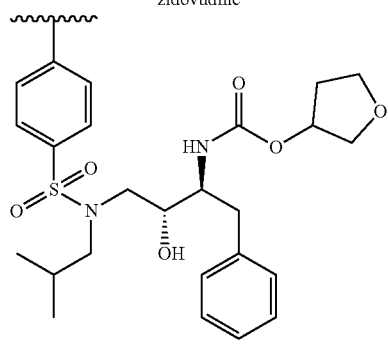

amprenavir

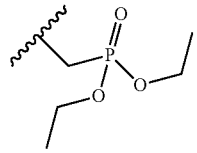

acrylic phosphonate

In other words, this invention consists of HIV inhibitor compounds obtained through molecular hybridization with zidovudine, isatin, amprenavir and acyclic phosphonate derivative chains, where these chains are similar to those contained in the tenofovir structure. These new hybrid compounds contain the 1,2,3-triazole ring.

BACKGROUND OF THE INVENTION

The first clinical report of Acquired Immunodeficiency Syndrome—AIDS ("*Sindrome da Imunodeficiencia Humana*" in Portuguese) was issued in 1981, After confirming that Human Immunodeficiency Virus (HIV) was the retrovirus that constituted the etiological agent of this disease, many research projects focused seeking a cure for this syndrome. However, no active ingredient has been identified so far that can eradicate the virus from the body.

However, major advances have been achieved in the treatment of AIDS through the development of new antiretroviral compounds. The therapeutic arsenal currently, has 28 medicines, divided into six different classes. Since 1996, treatment has deployed combinations of drugs of different antiretroviral classes in a "cocktail" that has become the standard, commonly known as Highly Active Antiretroviral Therapy (HAART). The introduction of this therapeutic regimen minimized the development of resistant virus A pioneer, Brazil was one of the first countries to provide free access and distribution to HAART. Medications were channeled to HIV-positive patients through Brazil's Unified National Health System (SUS) under the Medications Policy encompassed by the National Program for Sexually-Transmitted Diseases and AIDS (STD/AIDS), underpinned by Federal Law No 9,313/96. Today, Brazil produces generic antiretroviral medications.

AIDS still remains a global health problem that challenges the scientific community. In 2014, the latest epidemiological bulletin published by the Ministry of Health estimated that 734,000 people were living with HIV/AIDS in Brazil. Access to HAART has significantly increased the survival times of these patients, with fewer deaths. Worldwide, 1, 7 million people died from this disease in 2011, 24% fewer than the peak figure of about 2.3 million cases in 2005.

The etiological agent that transmits this disease is HIV, a retrovirus with two main serotypes: HIV-1 and HIV-2. The most widespread is HIV-1. causing most cases of AIDS. Limited more to West Africa, HIV-2 has lower mutation, virulence and transmissibility rates, replicating more slowly in the human body.

The goal of therapy is to promote the effective reduction of viral replication. The best strategy for achieving this purpose is to use the HAART regimen, as combinations of different drugs inhibit various stages of the replication cycle, significantly decreasing the viral load in the body. Associations may be administered as cocktails (different medications taken simultaneously) or through fixed-dose combined (FDC) Formulations. During the past few years, the use of FDCs has increased, driven by economic advantages for pharmaceutical companies, in parallel to enhanced compliance with treatment, HIV-positive patients.

The drugs approved for AIDS treatment are divided into six classes, by viral replication inhibition point: entry inhibitors (EI); fusion inhibitors (FI); nucleoside reverse transcriptase inhibitors (NRTI); non-nucleoside reverse transcriptase inhibitors (NNRTIs); integrase inhibitors (II) and protease inhibitors (PI).

Tenofovir (TDF) and zidovudine (AZT) are used more for antiretroviral treatment with NRTIs. Among the protease inhibitors (PI), amprenavir (APV) has the longest half-life in the body, in addition to high water solubility and good lipophilicity. However, the use of APV was discontinued in 2003, after the approval of fosamprenavir.

However, despite the existence of this entire therapeutic arsenal, many challenges still remain:
  Long duration of the dosing regimen;
  Cardiometabolic side effects and other toxic aspects that occur over the long term;
  Genetic diversity of the virus and the emergence of drug resistance;
  New transmissions from retroviral reservoirs in monkeys;
  High transmissivity rate, including strains resistant to available drugs, remaining constant in many parts of the world.

All these factors have boosted the amount of research in this field, seeking new compounds with known or innovative mechanisms of action. A strategy for obtaining new therapeutic options faster is synthesizing molecules that who structures already contain a unit with recognized antiretroviral activity recognized. With heterocyclic nuclei, isatins and triazoles are considered good prototypes in the quest for substances with potential antiretroviral activity.

According to Morphy R.; Rankovic, Z. (Designed multiple ligands. An emerging drug discovery paradigm. Journal of Medicinal Chemistry, vol. 48, 21, page 6523-6543, 2005) hybrid molecule synthesis been used in order to seek new drugs. Hybrid compounds may be obtained through docking substances with established pharmacological activity and toxicity, and the resulting systems are frequently endowed with enhanced biochemical characteristics, compared to their previous compounds.

There are no references in the literature to compounds derived from Formula 1 isatin used as antiretroviral drugs, with descriptions of only some imine derivatives obtained from this system such as:
  Substances obtained from the reaction with lamivudine as prodrugs (SRIRAM, D.; YOGEESWARI, P.; GOPAL, G. Synthesis, anti-HIV and antitubercular activities of lamivudine prodrugs. European Journal of Medicinal Chemistry, v. 40, page 1373 to 1376, 2005);
  Compounds obtained from the reaction with sulfonamides as integrase inhibitors (II) (Selvam, P.; Murugesh, N.; Chandramohan, M.; DEBYSER, Z.; Witvrouw, M. Design, Synthesis and anti-HIV activity of novel isatin-sulphonamides. Indian Journal of Pharmaceutical Sciences, vol. 70, 6, pages 779-782, 2008. Selvam, P.; Murugesh, N.; Chandramohan, M.; HOMBROUCK, A.; VERCAMMEN, J.; ENGELBORGHS, Y.; DEBYSER, Z.; WITRROUW M. Inhibition of integrase and HIV replication activity by 4-[{1, 2-dihydro-2-oxo-3H-indol-3-ylidene) amino]-N-(4,6-dimethyl-2-pyrimidinyl)-benzenesulfonamide and derivatives. International Journal of Drug Design and Discovery, Vol. 1, 2, page 161-168, 2010);
  Chemical structures synthesized through the reaction with thiosemicarbazide as reverse transcriptase inhibitors (RTI) (Teitz, Y.; BARKO, N.; Abramoff, M.; Ronen, D. Relationships between structure and activity of antiretroviral thiosemicarbazone derivatives. Chemotherapy, v. 40, 3, page 195-200, 1994.

The literature describes the use of a 3-(cyclopropylethanol)-3-hydroxy-indolin-2-one as RT inhibitors with Formula II replaced by bulky groups at the N−1 position on the indolin)-2-one ring that resulted in the loss of RT activity (BOECHAT, N.; Kover, W B; BONGERTZ, V.; Bastos, M M; ROMEIRO N. C; Azevedo, M L G; Wollinger, W. Design, synthesis and pharmacological evaluation of HIV-1 reverse transcriptase inhibition of new indolin-2-ones. Medicinal Chemistry, Vol. 3, No 6, page 533-542, 2007). In Formula II compounds, it was noted that the insertion of bulky groups at N−1 had no adverse effects on RT inhibitory activity.

There are no reports in the literature on the use of 3,3-difluoro-indolin-2-one derivative Formula III compound as antiretroviral medication, obtained from the reaction with isatin. This presents anti-inflammatory, analgesic, anticonvulsant, anti-Alzheimer, antidepressant, antipsychotic, anxiolytic and anti-Parkinson activities (BOECHAT, N.; Kover, W B; BONGERTZ, V.; Bastos, M M; ROMEIRO N. C; Azevedo, MLG; Wollinger, W. Design, Synthesis and Pharmacological Evaluation of HIV-1 reverse transcriptase inhibition of new indolin-2-ones Medicinal Chemistry, Vol 3, No 6, pages 533-542, 2007; WO 2006008067, 2006; and WO 2015012400, 2015).

This invention comprises the development of multi-target compounds that, in addition to being active, do not present the same problems as seen in drugs currently used to treat the disease. Furthermore, these compounds act as inhibitors of the hepatitis B virus (HBV), which is one of the main co-infections diagnosed in HIV-positive patients.

The hepatitis B virus (HBV) is a chronic infection that affects over 350 million people worldwide remains a threat to global public health (El-Serag, H B Epidemiology of hepatitis and Hepatocellular Viral Carcinoma. Gastroenterology, vol. 142, pages 1264-1273, 2012; Seeger C; Mason, W S; ZOULIM, F.; Hepadnaviruses In: Knipe, D M; HOWLEY, A M (eds) Fields Virology, Philadelphia, Pa.: Lippincott Williams & Wilkins, 2977 pages 2977-3029, 2007). HBV is a member of the hepadnaviridae family (Seeger C; Mason, W S; ZOULIM, F.; Hepadnaviruses In: Knipe, D M; HOWLEY, A M (eds) Fields Virology, Philadelphia, Pa.: Lippincott Williams & Wilkins, pages 2977-3029, 2007). At 3.2-kb, the replication of its viral genome depends on a polymerase encoded by this genome. This viral polymerase is a specialized reverse transcriptase (RT). Thus, similar to HIV RT, HBV TR uses pregenomic RNA (pgRNA) as a template for synthesizing a negative strand of viral DNA (Seeger C; Mason, W S; ZOULIM, F.; Hepadnaviruses In: Knipe, D M.; HOWLEY, A M (eds) Fields Virology, Philadelphia, Pa.: Lippincott Williams & Wilkins, pages 2977-3029, 2007; Hu, J.; Seeger, C. Expression and characterization of hepadnavirus reverse transcriptases Enzymoly Methods, Vol. 275, pages 195-208, 1996). Negative strand DNA synthesis is used for positive-stranded DNA. Hepadnavirus RT consists of four domains. Located in the C-terminal, the catalytic domain presents 78% homology with HIV RT. This consequently justifies the fact that new HIV RT inhibitors also exhibit activity against HBV RT (LANFORD, RE; NOTVALL, G, LEE, H.; BEAMES, B. Transcomplementation of nucleotide priming and reverse transcription between independently expressed TP and RT domains of the hepatitis B virus reverse transcriptase. Journal of Virology, vol 71, 2996-3004, 1997; Seeger C; Mason, W S; ZOULIM, F.; Hepadnaviruses In: Knipe, D M; HOWLEY, P M (.eds) Fields Virology, Philadelphia, Pa.: Lippincott Williams & Wilkins, pages 2977-3029, 2007; Hu, J.; Seeger, C. Expression and characterization of hepadnavirus reverse transcriptases Enzymoly Methods, vol 275, p 195.-208, 1996).

DESCRIPTION OF THE INVENTION

The main purpose of this invention comprises compounds derived from isatin, also known as Formulae I, II or III indolin derivatives.

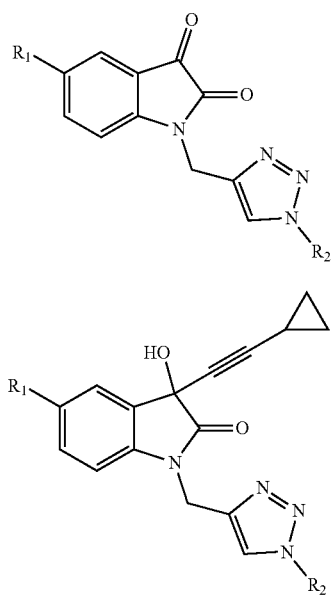

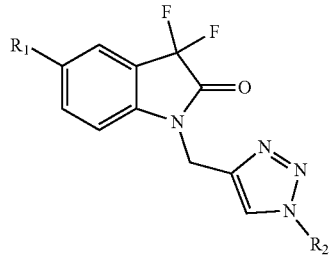

whereby in Formulae I, II and III:
$R_1$ is selected from H, $CH_3$ or Cl
$R_2$ is selected from one of the following radicals: zidovudine, amprenavir or an acyclic phosphonate chain, as shown below.

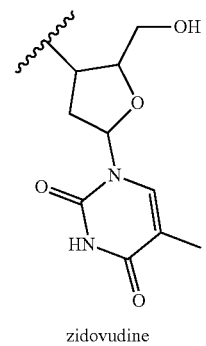

zidovudine

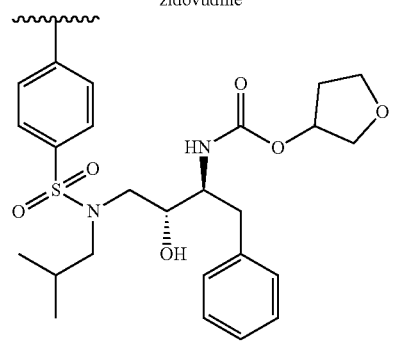

amprenavir

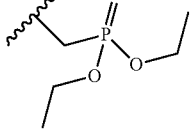

acrylic phosphonate

Another purpose of the invention relates to the use of Formulae I, II and III compounds for the treatment of AIDS and HBV HBV-HIV co-infection, A further purpose of the invention is the method of treatment using Formulae I, II and III compounds.

When each of the isatin-derived Formulae I, II and III compounds are substituted by the $R_1$ and $R_2$ radicals, nine compounds are obtained. Through replacing I, II and III by the radicals and $R_2$, all 27 compounds are obtained. For a better understanding of this invention, the nine compounds are identified by letters of the alphabet, between "a" and "i".

Hence, molecules obtained from Formula I are called I(a-i); those resulting from Formula II are called II(a-i); and those from Formula III are III(a-i).

Molecules I(a-i), II(a-i) and III(a-i) are innovative compounds with high HIV-1 reverse transcriptase (RT) inhibition percentages and low toxicity, which may be used as novel options for the treatment of HIV patients.

During the past few years, hybrid molecule synthesis has been used as a strategy for discovering new drugs. Hybrids may be obtained by docking substances with established pharmacological activity and toxicity; very often, the resulting systems are endowed with enhanced biochemical characteristics compared to their previous compounds. However, the new compounds may have completely different mechanisms of action from their compounds of origin.

The compounds constituting this invention comprise two parts, with the first part consisting of new hybrid molecules derived from Formulae I(a-i), II(a-i) and III(a-i) isatin, with no reports in the literature on their use as antiretroviral medications.

Hence, isatin was used for the 1(i-a) compound; a 3-(cyclopropylethanol)-3-hydroxy-indolin-2-one derivative was used for compound II(i-a); and a 3,3-difluoro-indolin-2-one derivative was used for Compound III(a-i); with compounds II(a-i) and III(a-i) obtained from the reaction with isatin.

The second part of the chemical structure of new hybrid molecules I(i-a), II(a-i) and III(i-a) may be formed by $R_2$ radicals, which comprise zidovudine (AZT), amprenavir (APV), or an acyclic phosphonate chain similar to that in the structure of tenofovir disoproxil fumarate (TDF).

AZT and TDF are representatives of the nucleoside reverse transcriptase inhibitors (NRTI) and nucleotide reverse transcriptase inhibitors (NtRTI) class, while PVA is a representative of protease inhibitors (PI). AZT and VPA were fully inserted in the isatin-derived Formulae I, II and III chemical structures; however, the innovative differential new compounds l(i-a), II(a-i) and III(a-i) consists of inhibiting different enzymes involved in the viral replication cycle, which does not occur with the compounds of origin. In terms of a similar acyclic phosphonate chain in the TDF, it is noteworthy that the acyclic carbohydrate part was removed in the new hybrid molecules, which is essential for biological activity in the original drug.

It is emphasized that. in this invention, Compound I(a-i) was obtained from the reaction with isatin, used as an antiretroviral agent.

Derived from 3-(cyclopropylethanol)-3-hydroxy-indolin)-2-one and used as a TR inhibitor, Compound II(a-i) was obtained from the reaction with isatin. The innovative advantage of these compounds consists of the substitution of bulky groups at the N–1 position on the indolin-2-one ring while maintaining the TR activity.

For Compound III(a-i), its 3,3-difluoro-indolin-2-one derivative obtained from the reaction with isatin was used for the first time as an antiretroviral agent.

Although Compounds I(a-i), II(a-i) and III(a-i) include AZT in their structure, as well as APV and an acyclic phosphonate chain similar to that of TDF, they are endowed with a major comparative advantage in terms of innovation and the inhibition of other enzymes involved in the viral and HBV TR replication cycle, making them multi-target substances. This fact is extremely important, as the use of these compounds can eliminate problems arising from the use of combinations of inhibitors in different classes, which generally occurs through associations administered as cocktails (assorted medications taken simultaneously), or fixed-dose combination (FDC) formulations.

Compliant with the nomenclature established by the International Union of Pure and Applied Chemistry (IUPAC), the Formula I compounds are identified as follows:

1-((1-(2-(hydroxymethyl)-5-(5-methyl-2.4-dioxo-3.4-dihydropyrimidine-1(2H)-yl)tetrahydrofuran-3-yl)-1H-1,2,3-triazole-4-yl)methyl)indolin-2.3-dione;

1-((1-(2-(hydroxymethyl)-5-(5-methyl-2.4-dioxo-3.4-dihydropyrimidine-1(2H yl)tetrahydrofuran-3-yl)-1H-1,2,3-triazole-4-yl)methylindolin-2.3-dione;

5-chloro-1-((1-(2-(hydroxymethyl)-5-(5-methyl-2.4-dioxo-3.4-dihydropyrimidine-1(2H)-yl)tetrahydrofuran-3-yl)-1H-1,2,3-triazole-4-yl)methyl)indolin-2.3-dione;

tetrahydrofuran-3-yl ((2S)3R)-4-(4-(4-((2.3-dioxoindolin-1-yl)methyl)-1H-1,2,3-triazole-1-yl)-N-isobutylphenylsulfonamide)-3-hydroxy-1-phenylbutan-2-yl) carbamate;

tetrahydrofuran-3-yl ((2S,3R)-3-hydroxy-4-(N-isobutyl-4-(4-((5-methyl-2.3-dioxoindolin-1-yl)methyl)-1H-1,2,3-triazole-1-yl)phenylsulfonamide)-1=phenylbutan-2-yl) carbamate;

tetrahydrofuran-3-yl ((2 S13R)-4-(4-(4-((5-chloro-2.3-dioxoindolin-1-yl)methyl)-1H-1,2,3-triazole-1-yl)-N-isobutylphenylsulfonamide)-3-hydroxy-1-phenylbutan-2-yl) carbamate;

diethyl ((4-((2.3-dioxoindolin-1-yl)methyl)-1H-1,2,3-triazole-1-yl)methyl) phosphonate;

diethyl ((4-((5-methyl-2.3-dioxoindolin-1-yl)methyl)-1H-1,2,3-triazole-1-yl)methyl) phosphonate;

diethyl ((4-((5-chloro-2.3-dioxoindolin-1-yl)methyl)-1H-1,2,3-triazole-1-yl)methyl) phosphonate.

Compliant with the nomenclature established by the International Union of Pure and Applied Chemistry (IUPAC), the Formula II compounds are identified as follows:

1-(4-(4-((3-(cyclopropylethanol)-3-hydroxy-2-oxoindolin-1-yl)methyl)-1H-1,2,3-triazole-1-yl)-5-(hydroxymethyl)tetrahydrofuran-2-yl)-5-methylpyrimidine-2.4(1H,3H)-dione;

1-(4-(4-((3-(cyclopropylethanol)-3-hydroxy-5-methyl-2-oxoindolin-1-yl)methyl)-1H-1,2,3-triazole-1-yl)-5-(hydroxymethyl)tetrahydrofuran-2-yl)-5-methylpyrimidine-2.4(1H,3H)-dione;

1-(4-(4-((5-chloro-3-(cyclopropylethanol)-3-hydroxy-2-oxoindolin-1-yl)methyl)-1H-1,2,3-triazole-1-yl)-5-(hydroxymethyl)tetrahydrofuran-2-yl)-5-methylpiri-2.4(1H,3H)-dione;

tetrahydrofuran-3-yl ((2 S,3R)-4-(4-(4-((3-(cyclopropylethanol)-3-hydroxy-2-oxoindolin-1-yl)methyl)-1H-1,2,3-triazole-1-yl)-N-isobutylphenylsulfonamide)-3-hydroxy-1-phenylbutan-2-yl)carbamate;

tetrahydrofuran-3-yl ((2 S,3R)-4-(4-(4-((3-(cyclopropylethanol)-3-hydroxy-5-methyl-2-oxoindolin-1-yl)methyl)-1H-1,2,3-triazole-1-yl)-N-isobutylphenylsulfonamide)-3-hydroxy-1-phenylbutan-2-yl)carbamate;

tetrahydrofuran-3-yl ((2S,3R)-4-(4-(4-((5-chloro-3-(cyclopropylethanol)-3-hydroxy-2-oxoindolin-1-yl)methyl)-1H-1,2,3-triazole-1-yl)-N-isobutylphenyl sulfonamide)-3-hydroxy-1-phenylbutan-2-yl) carbamate;

diethyl ((4-((3-(cyclopropylethanol)-3-hydroxy-2-oxoindolin-1-yl)methyl)-1H-1,2,3-triazole-1-yl)methyl) phosphonate;

diethyl ((4-((3-(cyclopropylethanol)-3-hydroxy-5-methyl-2-oxoindolin-1-yl)methyl-1,2,3-triazole-1-yl)methyl) phosphonate;

diethyl ((4-((5-chloro-3-(cyclopropylethanol)-3-hydroxy-2-oxoindolin-1-yl)methyl)-1H-1,2,3-triazole-1-yl)methyl) phosphonate.

Compliant with the nomenclature established by the International Union of Pure and Applied Chemistry (IUPAC), the Formula III compounds are identified as follows:

1-(4-(4-((3,3-difluor-2-oxoindolin-1-yl)methyl)-1H-1,2,3-triazole-1-yl)-5-(hydroxymethyl)tetrahydrofuran-2-yl)-5-methylpyrimidine-2.4(1H,3H)-dione;

1-(4-(4-((3,3-difluor-5-methyl-2-oxoindolin-1-yl)methyl)-1H-1,2,3-triazole-1-yl)-5-(hydroxymethyl)tetrahydrofuran-2-yl)-5-methylpyrimidine-2.4(1H,3H)-dione;

1-(4-(4-((5-chloro-3.3-difluor-2-oxoindolin-1-yl)methyl)-1H-1,2,3-triazole-1-yl)-5-(hydroxymethyl)tetrahydrofuran-2-yl)-5-methylpyrimidine-2.4(1H,3H)-dione, tetrahydrofuran-3-yl ((2S13R)-4-(4-(4-((3,3-difluor-2-oxoindolin-1-yl)methyl)-1H-1,2,3-triazole-1-yl)-N-isobutylphenylsulfonamide)-3-hydroxy-1-phenylbutan-2-yl) carbamate;

tetrahydrofuran-3-yl ((2S,3R)-4-(4-(4-((3,3-difluor-5-methyl-2-oxoindolin-1-yl)metH)-1H-1,2,3-triazole-1-yl)-N-isobutylphenyl sulfonamide)-3-hydroxy-1-phenylbutan-2-yl) carbamate;

tetrahydrofuran-3-yl ((2S,3R)-4-(4-(4-((5-cloro-3.3-difluor-2-oxoindolin-1-yl)methyl)-1H-1,2,3-triazole-1-yl)-N-isobutylphenylsulfonamide)-3-hydroxy-1-phenylbutan-2-yl) carbamate;

diethyl ((4-((3,3-difluor-2-oxoindolin-1-yl)methyl)-1H-1,2,3-triazole-1-yl)methyl) phosphonate;

diethyl ((4-((3,3-difluor-5-methyl-2-oxoindolin-1-yl)methyl)-1H-1,2,3-triazole-1-yl)methyl) phosphonate;

diethyl ((4-((5-chloro-3.3-difluor-2-oxoindolin-1-yl)methyl)-1H-1,2,3-triazole-1-yl)methyl) phosphonate.

Molecular docking studies of these new compounds were crucial for defining possible enzyme inhibition points in the viral replication cycle. The docking results for these synthesized molecules were based on evaluation and function ratings on a scoring grid, grounded on terms unconnected to the force field and the internal energy function, which is intended to measure internal collisions during twist optimization. The latter always has a positive value, which indicates a penalty resulting from collisions in each pose.

These functions are based on force field components, with approximate interaction energies composed of van der Waals forces and electrostatic components. The final score for the compounds is given by the sum of the grid score internal and energy values. The result should be as low as possible, because low values indicate a stable system, with less energy between the ligand-receptor complex and a probable interaction.

The viral RT enzyme is extremely important in HIV replication, as it encodes the virus DNA molecule from its RNA. The enzyme is derived from a polyprotein encoded by the virus, processed by the viral protease.

The 1Q05 PDB code structure (TUSKE, S.; SARAFIANOS, S. G.; CLARK, J. R. A. D.; DING, J.; NAEGER, L K.; WHITE, K. L.; MILLER, M. D.; GIBBS, C S., BOYER, P. L; CLARK, P.; WANG, G.; GAFFNEY, B. L; JONES, R. A.; JERINA, D. M.; HUGHES, S. H.; ARNOLD, E. Structures of HIV-1 RTDNA complexes before and after incorporation of the anti-AIDS drug tenofovir. Nature Structural & Molecular Biology, v. 11, page 469-474, 2004), complexed with tenofovir, was chosen to provide a favorable conformation for docking molecules at the active RT site. The docking simulations were preceded by redocking, which consists of a process docking the ligand on the native receptor. It is used to assess the replicability of the docking program For a better understanding of this invention, codes are presented below for each synthesized molecule, with a definition of each of the $R_1$ and $R_2$ radicals.

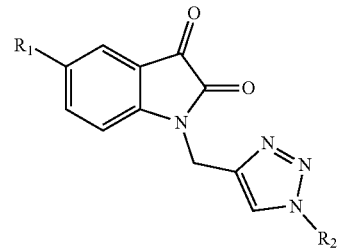

Ia: $R_1$ = H; $R_2$ = zidovudine
Ib: $R_1$ = $CH_3$; $R_2$ = zidovudine
Ic: $R_1$ = Cl; $R_2$ = zidovudine
Id: $R_1$ = H; $R_2$ = amprenavir
Ie: Id: $R_1$ = $CH_3$; $R_2$ = amprenavir
If: $R_1$ = H; $R_2$ = acyclic phosphonate
Ig: $R_1$ = $CH_3$; $R_2$ = acyclic phosphonate
Ih: $R_1$ = Cl; $R_2$ = acyclic phosphonate

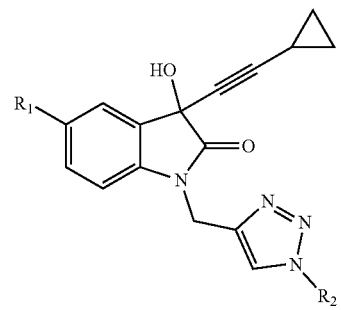

IIa: $R_1$ = H; $R_2$ = zidovudine
IIb: $R_1$ = $CH_3$; $R_2$ = zidovudine
IIc: $R_1$ = Cl; $R_2$ = zidovudine
IId: $R_1$ = H; $R_2$ = acyclic phosphonate
IIe: Id: $R_1$ = $CH_3$; $R_2$ = acyclic phosphonate
IIf: $R_1$ = H; $R_2$ = acyclic phosphonate

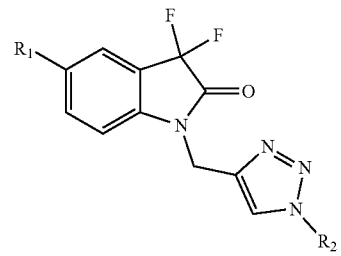

IIIa: $R_1$ = H; $R_2$ = zidovudine
IIIb: $R_1$ = $CH_3$; $R_2$ = zidovudine
IIIc: $R_1$ = Cl; $R_2$ = zidovudine
IIId: $R_1$ = H; $R_2$ = acyclic phosphonate
IIIe: Id: $R_1$ = $CH_3$; $R_2$ = acyclic phosphonate
IIIf: $R_1$ = H; $R_2$ = acyclic phosphonate The results of docking the end-molecules on the 1T05 structure (RT with tenofovir) are described in Table 1.

TABLE 1

DOCKING RESULTS FOR THE END-MOLECULES ON THE 1T05 STRUCTURE

| Molecules | Grid Score | Internal Energy | Grid Score + Int_Energy | Hydrogen Ligands | Interactions with Residues |
|---|---|---|---|---|---|
| Ia | −51.87 | 10.88 | −40.99 | 1 | ARG72, GLN151 |
| Ib | −54.72 | 7.88 | −46.84 | 2 | LYS219, LEU228, GLY231, $Mg^{+2}$ |
| Ic | −56.52 | 17.45 | −39.07 | 0 | ARG72, LYS219, $Mg^{+2}$ |
| Id | −71.50 | 21.00 | −50.50 | 1 | ARG72, ALA114, LYS219, $Mg^{+2}$ |
| Ie | −70.84 | 19.28 | −51.56 | 0 | LYS65, ARG72, $Mg^{+2}$ |
| If | −55.87 | 8.69 | −47.18 | 1 | ARG72, ALA114, TYR115, $Mg^{+2}$ |
| Ig | −56.14 | 6.38 | −49.76 | 0 | ARG72, LYS219, $Mg^{+2}$ |
| Ih | −56.93 | 8.42 | −48.51 | 0 | ARG72, LYS219, $Mg^{+2}$ |
| IIa | −61.08 | 12.67 | −48.41 | 1 | LYS65, LEU228, LYS219, $Mg^{+2}$ |
| IIb | −60.34 | 12.12 | −48.22 | 1 | LYS65, LYS219, GLY231 |
| IIc | −59.96 | 14.26 | −45.70 | 1 | LYS65, LYS219, MET230 |
| IId | −60.87 | 6.47 | −54.40 | 3 | LYS65, ARG72, TYR115, $Mg^{+2}$ |
| IIe | −55.98 | 6.61 | −49.37 | 0 | LYS65, LYS219, $Mg^{+2}$ |
| IIf | −60.11 | 6.98 | −53.13 | 0 | $Mg^{+2}$ |
| IIIa | −55.18 | 16.77 | −38.41 | 3 | LYS65, ARG72, LYS219, $Mg^{+2}$ |
| IIIb | −51.62 | 10.26 | −41.36 | 1 | ARG72, LYS219, $Mg^{+2}$ |
| IIIc | −53.20 | 9.87 | −43.33 | 1 | ARG72, TYR115 |
| IIId | −53.72 | 8.74 | −44.98 | 0 | ARG72, LYS219, $Mg^{+2}$ |
| IIIe | −54.31 | 5.46 | −48.85 | 0 | ARG72, LYS219, $Mg^{+2}$ |
| IIIf | −57.27 | 14.81 | −42.46 | 2 | ARG72, $Mg^{+2}$ |

Dockings were then undertaken with the PDB 4G1Q structure (rilpivirine) (KURODA, D. G.; BAUMAN, J. D.; CHALLA, J. R.; PATEL, D.; TROXLER, T.; DAS, K.; ARNOLD, E.; HOCHSTRASSER, R. M. Snapshot of the equilibrium dynamics of a drug bound to HIV-1. Nature Chemistry, v. 5, page 174 to 181, 2013), which is the RT allosteric site. Before starting the simulations, was performed with rilpivirine PDB (T27) (http://www.csb.org/pdb/ligand/ligandsummary.do?hetld=T27, a non-nucleoside RT inhibitor. When binding to the RT allosteric site, it causes a conformational change in the enzyme structure, leading to a decrease in affinity through the natural nucleotides. The docking results for all the synthesized end-molecules in the 4G1Q structure are described in Table 2.

TABLE 2

DOCKING RESULTS FOR ALL THE SYNTHESIZED END-MOLECULES IN THE 4G1Q STRUCTURE

| Molecules | Grid Score | Internal Energy | Grid Score + int_Energy | Hydrogen Ligands | Interactions with Residues |
|---|---|---|---|---|---|
| Ia | −41.60 | 6.91 | −34.69 | 3 | $H_2$ |
| Ib | −46.48 | 18.93 | −27.55 | 4 | LYS101, $H_2$ |
| Ic | −47.69 | 20.43 | −27.26 | 4 | LYS101, $H_2$ |
| Id | −59.44 | 20.29 | −39.15 | 0 | — |
| Ie | −54.94 | 22.83 | −32.11 | 0 | — |
| If | −51.61 | 15.67 | −35.94 | 1 | LYS101, TYR181 |
| Ig | −51.02 | 13.35 | −37.67 | 1 | LYS103, TRP229, $H_2$ |
| Ih | −53.16 | 16.09 | −37.07 | 2 | TYR181, TRP229, $H_2$ |
| IIa | −15.29 | 20.36 | 5.07 | 2 | LYS103 |
| IIb | −2.10 | 19.57 | 17.47 | 0 | — |
| IIc | — | — | — | — | — |
| IId | −20.25 | 24.43 | 4.18 | 3 | LYS101, LYS103, $H_2$ |
| IIe | −29.52 | 23.02 | −6.50 | 3 | LYS101, LYS103, $H_2$ |
| IIf | −62.10 | 16.82 | −45.28 | 0 | TYR181, TRP229 |
| IIIa | −28.31 | 12.09 | −16.22 | 3 | LYS101, LYS103, $H_2$ |
| IIIb | −31.95 | 14.61 | −17.34 | 2 | LYS101, LYS103, ILE178 |
| IIIc | −30.12 | 16.84 | −13.28 | 2 | LYS101, LYS103 |
| IIId | −47.93 | 15.45 | −32.48 | 1 | TYR181, TRP229, $H_2$ |
| IIIe | −50.13 | 17.84 | −32.29 | 2 | TYR181, TRP229, $H_2$ |
| IIIf | −51.75 | 23.87 | −27.88 | 1 | TYR181, TRP229, $H_2$ |

The final docking analyses were performed on the PDB 3NU3 structure (SHEN, C. H.; WANG, Y. F.; KOVALEVSKY, A. Y.; HARRISON, R. W.; WEBER, I. T. Amprenavir complexes with HIV1 protease and its drug-resistant mutants altering hydrophobic clusters. Febs Journal, v. 277, page 3699-3714, 2010) which represents the protease. Redocking on the 3NU3 structure (amprenavir) was performed by removing water molecules from the protease crystal structure in order to simplify the docking procedure. The RMSD docking pose was satisfactory at below 1.0 A, with a grid score of −81,54 and internal energy at 19.25. HIV-1 protease is a homodimer containing a catalyst site with the ASP-THR-GLY triad present, which is a characteristic of the aspartic proteases. The crystallographic pose presented interactions with the ASP25, ASP30, ASP125, GLY127 and ASP130 residues, while the redocking pose presented interactions with the ASP25, ASP30, ASP124, GLY126 and ASP129 residues. The docking results for all the end-molecules in the PDB 3NU3 structure are described in Table 3.

TABLE 3

DOCKING RESULTS FOR ALL END-MOLECULES IN THE 3NU3 STRUCTURE

| Molecule | Grid Score | Internal Energy | Grid Score + Int_Energy | Hydrogen Ligands | Interactions with Residues |
|---|---|---|---|---|---|
| Ia | −63.62 | 16.81 | −46.81 | 1 | ASP29 |
| Ib | −63.01 | 21.88 | −41.13 | 1 | GLY148 |
| Ic | −61.60 | 19.58 | −42.02 | 1 | GLY148 |
| Id | −69.71 | 22.60 | −47.11 | 1 | ILE50 |
| Ie | −64.33 | 18.24 | −46.09 | 4 | ARG8, ILE50, PRO81, $H_2$ |
| If | −54.05 | 5.09 | −48.96 | 2 | ARG8, ILE50, $H_2$ |
| Ig | −55.26 | 9.54 | −45.72 | 2 | $H_2$ |
| Ih | −56.05 | 7.38 | −48.67 | 4 | $H_2$ |
| IIa | −58.51 | 22.72 | −35.79 | 1 | GLY48 |

TABLE 3-continued

DOCKING RESULTS FOR ALL END-MOLECULES IN THE 3NU3 STRUCTURE

| Molecule | Grid Score | Internal Energy | Grid Score + Int_Energy | Hydrogen Ligands | Interactions with Residues |
|---|---|---|---|---|---|
| IIb | −46.75 | 14.09 | −32.66 | 8 | GLY27, ARG108, GLU134, H$_2$ |
| IIc | −39.66 | 15.89 | −23.77 | 4 | LYS45, H$_2$ |
| IId | −60.56 | 8.98 | −51.58 | 1 | ASP29 |
| IIe | −63.09 | 12.81 | −50.28 | 2 | GLY127, ASP129 |
| IIf | −64.90 | 6.30 | −58.60 | 1 | ARG8, ILE50 |
| IIIa | −63.26 | 22.72 | −40.54 | 0 | AR68 |
| IIIb | −62.42 | 14.06 | 48.36 | 2 | ASP130, H$_2$ |
| IIIc | −59.61 | 18.32 | −41.29 | 1 | ARG108, H$_2$ |
| IIId | −56.31 | 7.09 | −49.22 | 2 | ARGS, ILE50, H$_2$ |
| IIIe | −53.80 | 7.39 | 46.41 | 3 | GLY48, H2 |
| IIIf | −57.75 | 14.06 | 43.69 | 2 | ARG8, ILE50, H$_2$ |

The analysis of the theoretical study of all the synthesized compounds showed that the best score results and more interactions with amino acid residues and ions were obtained in PDB 3NU3 (protease) and PDB 1Q05 (reverse transcriptase) structures. The score results for the active protease site are the most promising, with more hydrogen interactions than the two other sites studied. It may thus be considered that the synthesized substances act as multi-target molecules, as they can act at two separate viral enzyme sites.

The 27 new hybrid Formulae I(a-i), II(a-i) and III(a-i) were designed, synthesized and biologically evaluated, deriving from isatin IV (c) and the V, VII and IX (c) derivatives, with zidovudine (X), amprenavir (XI) and an acyclic phosphonate chain (XII) similar to that in the TDF structure. With the 1, 2,3-triazole ring in their structures obtained through click chemistry, these new hybrids were evaluated for their potential HIV-1 RT inhibitory activity. Compounds IV, V, VII, IX, X, XI and XII are shown in Scheme 1 below.

The synthesizing methodology used to prepare the Formula I(a-i) and III(a-i) compounds began with the preparation of the/V-alkylated derivatives of V and VII (c) isatin, followed by the click chemistry reaction for obtaining the triazole ring, as shown in Scheme 1. An additional step is performed for obtaining the III(a-i) products, which consists of the gem-defluoridation reaction of VI (c) isatin using diethylaminosulfur trifluoride (DAST) as the fluorinating agent.

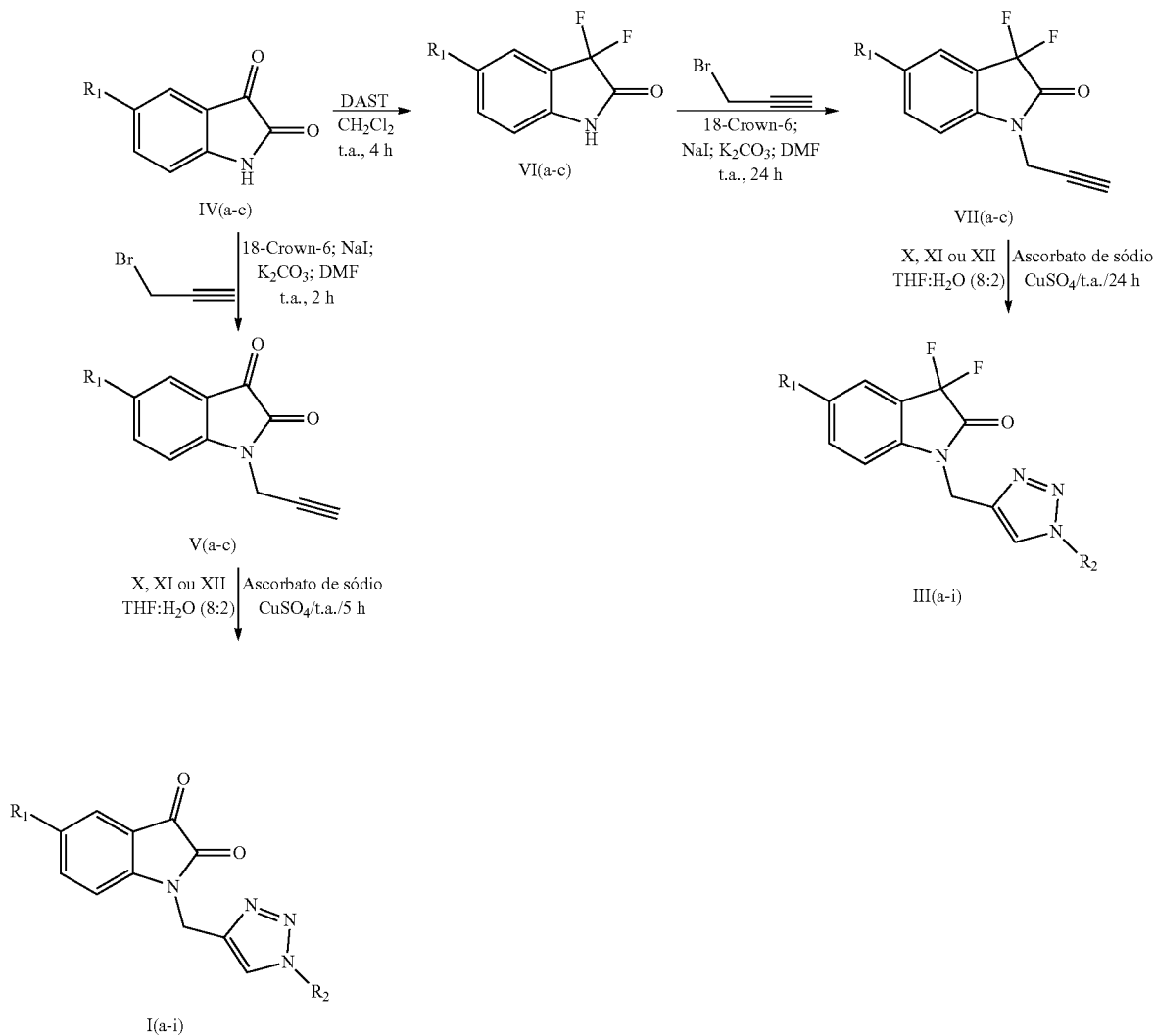

SCHEME 1

-continued

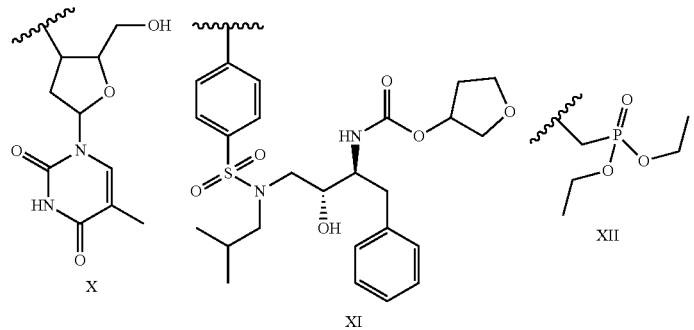

The preparation of analogs with Formulae I (df), II (df) and III (df) from isatin begins with obtaining drug XI azide. The methodology consists of a nucleophilic aromatic substitution reaction through diazonium salt formation (Scheme 2).

SCHEME 2

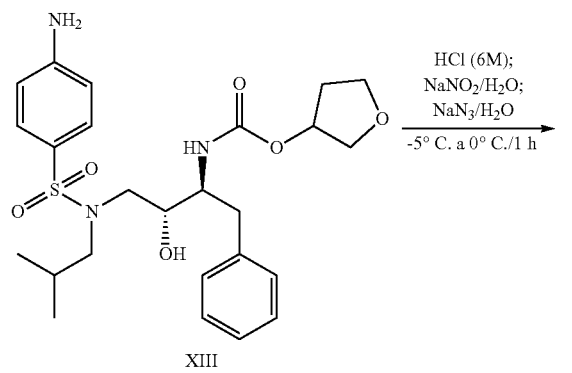

Initially, in order to synthesize analogs with Formulae I(g-i), II(g-i) and III(g-i), the preparation of azide phosphonate XII from diethyl p-toluenesulfonyloxymethyl phosphonate (XIV) is required, through a bimolecular nucleophilic substitution reaction (Scheme 3).

SCHEME 3

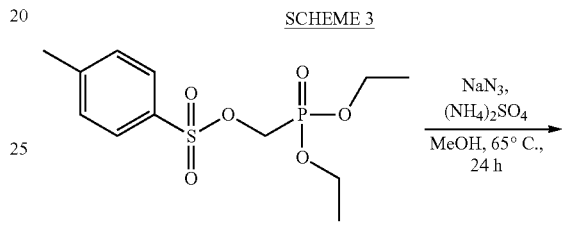

Preparation of the II(a-i) molecules begins with the reaction resulting from the addition of cyclopropylacetylene to the C-3 carbonyl of the IV (c) isatins. This is followed by N-alkylation of the VIII(c) derivatives in order to obtain the IX(c) intermediaries, which are then subjected to the cycloaddition reaction in order to obtain the planned II(a-i) end-substances. (Scheme 4).

SCHEME 4

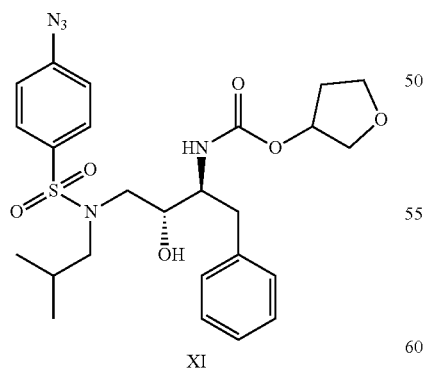
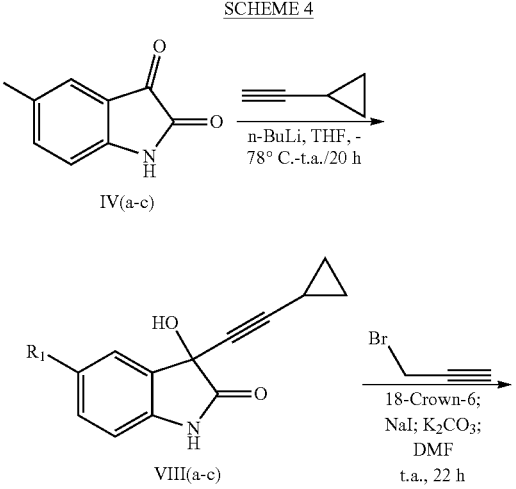

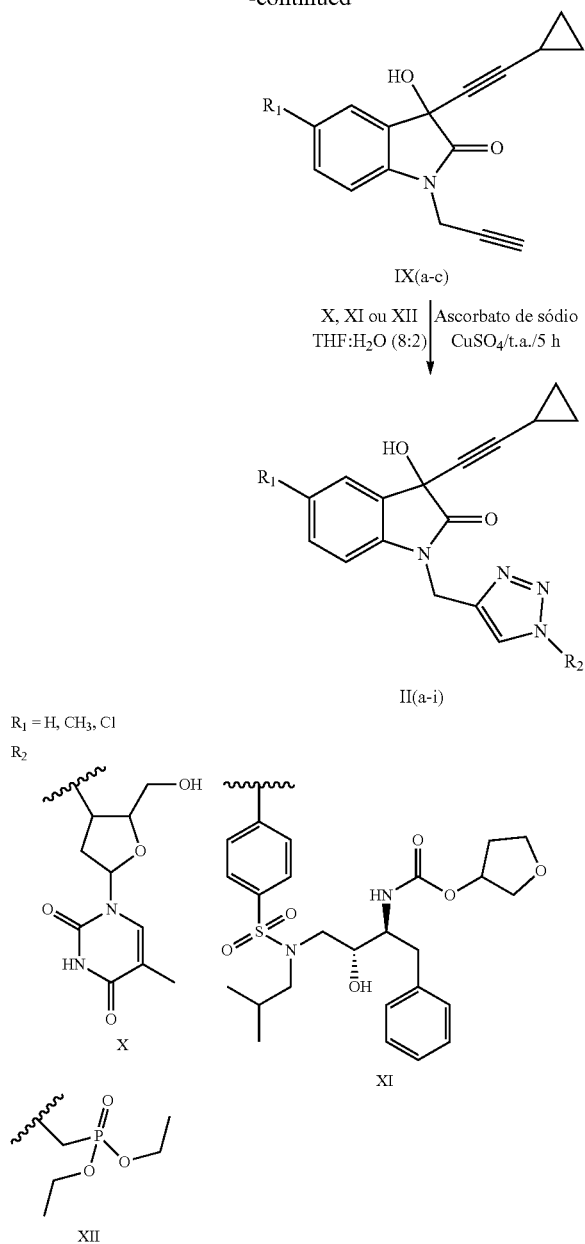

All the new compounds with Formulae I(a-i), II(a-i) and II(a-i) were characterized through nuclear magnetic resonancing (NMR) for the $^1H$, $^{13}C$, $^{19}F$, $^{31}P$ cores, infrared (IR), electrospray ionization mass spectrometry (ESI-MS), and high resolution mass spectrometry (HRMS). The purity of these new products was assayed through high-performance liquid chromatography.

EXAMPLES

Example 1—Antiretroviral Assessment

Preparation of Cells and Virus

The T-lymphocyte cell line (Suptl) was cultured in an RPMI 1640 medium (GIBICO). The cultures were supplemented with 10% Fetal Bovine Serum (SFB; HyClone, Logan, Utah, USA), 100 U/mL of penicillin and 100 μL/mL of streptomycin, and incubated at 37° C., in an atmosphere of 5% $CO_2$. Virus stocks were prepared using the methodology described by Souza and Denizot (SOUZA, T. M. L; RODRIGUES, D. Q.; FERREIRA, V. F.; MARQUES, I. P.; DE SOUZA, M. C. B. V.; FRUGULHETTI, I. C. P. P.; BOU-HABIB, D. C; FONTES, C. F. L. Characterization of HIV-1 enzyme reverse transcriptase inhibition by the compound 6-chloro-1.4-dihydro-4-oxo-1-(β-D-ribofuranosyl) quinoline-3-carboxylic acid through kinetic and in silico studies. Current HIV Research, v. 7, No 3, page 327-335, 2009. DENIZOT, F.; LANG, R. Rapid colorimetric assay for cell growth and survival. Modifications to the tetrazolium dye procedure giving improved sensitivity and reliability. The Journal of Immunological Methods, v. 89, No 2, page 271-277, 1986).

Cytotoxicity Assay

In a 96-well microplate (1×104/well), the Suptl cells were treated with different concentrations of the substances for 72 hours. They were then run through an MTT assay (3-(4,5-dimethylazol-2-yl)-2.5-diphenyl tetrazolium bromide) in order to analyze cell induction infeasibility. MTT is a colorimetric method that measures mitochondrial dehydrogenase activity based on the ability of live cells to reduce 3-(4,5-methylazol-2-yl)-2.5-diphenyl tetrazolium bromide salt in the product. A 50 pL solution of 3-(4,5-dimethylthiazol-2-yl)-2.5-diphenyl tetrazolium bromide (1 mg/ml) (MTT, Sigma) was thus added to the cells, kept in Dulbecco's Modified Eagle's medium (DMEM) without serum. The MTT was removed after three hours and, after adding 50 pL of isopropanol acid (0.04N HCl in isopropanol), the optical density (OD) was determined using a wavelength range of 570 to 690 nm, according to KUO et al (KUO, Y. C; CHEN, C. C; TSA, W. J.; HO, Y. H. Regulation of type 1 herpes simplex virus replication in vero cells by Psychotriaserpens: relationship to gene expression, DNA replication, and protein synthesis. Antiviral Research, v. 51, No 2, pages 95 to 109, 2001). The dye coloring has different optical densities, depending on mitochondrial metabolism after treating cells with different concentrations of the new derivatives or the absence thereof. The 50% cytotoxic concentration (CC50) was calculated through linear regression analysis from the dose-response curve obtained from experimental data.

Reverse Transcriptase Inhibition Activity

The inhibitory activity of the substances on RTHXB2 DNA-dependent RNA polymerase (RDDP) was evaluated through using recombinant enzyme purified HIV-1. as described by Souza et al. (SOUZA, T. M. L; RODRIGUES, D. Q.; FERREIRA, V. F.; MARQUES, I. P.; DE SOUZA, M. C. B. V.; FRUGULHETTI, I. C. P. P.; BOU-HABIB, D. C; FONTES, C. F. L Characterization of HIV-1 enzyme reverse transcriptase inhibition by the compound 6-chloro-1.4-dihydro-4-oxo-1-(P-D-ribofuranosyl) quinoline-3-carboxylic acid through kinetic and in silico studies. Current HIV Research, v. 7, No 3, page 327-335, 2009). The RDDP activity was determined in 50 mM Tris HCl (pH 7.8), 6 mM $MgCl_2$, 1 mM dithiothreitol, 50 mM KCl, 5 μM dTTP, 80 mg/ml poly (rA) oligo (dT) template primer (Pharmacia, Piscataway, N.J., USA) and 3 U of enzyme (one unit is the enzyme concentration incorporating dTTP 1 mol per minute per mg of enzyme at 37° C. under standard conditions). The reaction isotope dilutions were prepared at 2 μCi of [3H] dTTP (49 Ci/mmol)/2,7μ dTTP. The reaction was initiated at 37° C., incubated for 30 minutes and halted with 0.5M EDTA. The precipitate was collected on Whatman 81 filter paper and washed with 0.1 M sodium phosphate. The incorporated nucleotides were measured by liquid scintillation. The 50% inhibitory concentration (Ciso) was determined by linear regression analysis of the dose-response curve obtained from experimental data. The polymerization reaction was conducted in the presence and absence of test substances, as well as the presence and absence of standards.

Example 2—Synthesis of Formula I(A-i) Compounds

Before presenting the synthesis of Formula I(a-i) compounds, it is necessary to describe the syntheses of the V(c) intermediaries that gave rise to them.

Synthesis of V(a-c) Compounds

Using a 50 mL mono-tube flask, were added 6.8 mmol of the corresponding IV(a-c) isatins (1 eq), 11 mmol of propargyl bromide (1.63 eq), 12.92 mmol of potassium carbonate (1.9 eq), 2.1 mmol of sodium iodide (0.32 eq) and 0.2 mmol of 18-crown-6 (0.04 eq) in 6 mL of anhydrous DMF. The medium was kept under magnetic stirring, at room temperature for 2 hours. The completion of the reaction was shown through TLC, using the hexane:ethyl acetate (7:3) elution system. In order to isolate the product, the reaction mixture was washed with 30 mL of DMF and vacuum filtered. The resulting liquid was evaporated to give a brown oil, which was extracted with chloroform (50 mL) and washed with water (3×25 mL). The organic phase was dried with anhydrous sodium sulfate and the solvent was removed by evaporation, with the resulting product being a reddish solid.

Compound va:
  Yield: 85%
  Mp: 144° C. to 146° C. (lit. 157° C. to 158° C.) (JORDAN, C. A.; WIECZERZAK, K. B.; KNISLEY, K. J.; KETCHA, D. M. Expedited microwave-assisted N-alkylation of isatins using DBU. Archive for Organic Chemistry, v. 2014, No 4, pages 183 to 192, 2014)
  CG/EM (70 eV, m/z, %): 129 (100); 185 (91); 102 (54); 90 (44); 128 (39)

Compound vb:
  Yield: 41%
  Mp: 149° C. to 151° C. (lit. 163° C. to 164° C.) (ZHUNGIETU, G. I.; ZORIN, L. M.; REKHTER, M. A. Recyclization of N-acetonylisatins to 2-acetylindole-3-carboxylic acids. Izvestiya Akademii Nauk Moldavskoi SSR, Bioiogicheskie i Khimicheskie Nauki, v. 2, pages 57 to 65, 1981)
  CG/EM (70 eV, m/z, %): 142 (100); 141 (92); 114 (71); 198 (62); 76 (53)

Compound vc:
  Yield: 80%
  Mp: 158° C. to 159° C. (lit. 155° C. to 156° C.) (ZHUNGIETU, G. I., ZORJN, L. M.; REKHTER, M. A. Recyclization of N-acetonylisatins to 2-acetylindole-3-carboxylic acids. Izvestiya Akademii Nauk Moldavskoi SSR, Biologicheskie i Khimicheskie Nauki, v. 2, pages 57 to 65, 1981)
  CG/EM (70 eV, m/z, %): 162 (100); 123 (76); 218 (58); 74 (51)

Synthesis of Compounds I(a-i)

Using a 50 mL mono-tube flask, were added 2.3 mmol of the corresponding V(a-c) acetylenes (1.3 eq), 1.8 mmol of the X, XI or XII azides (1 eq), 0.1 mmol of sodium ascorbate (0.1 eq), 0.1 mmol of copper sulphate (0.06 eq) and 5 mL of a THF mixture with water (8:2). The reaction was kept under magnetic stirring at room temperature for 5 hours, with completion indicated by TLC through the hexane:ethyl acetate (3:7) elution system. At the end of the reaction, 30 mL of water was added, and the medium was extracted with $CHCl_3$ (3×50 mL). The organic phase was dried with anhydrous sodium sulfate, filtered and evaporated. The end-products were purified through a chromatography column, using the hexane:ethyl acetate (3:7) elution system.

Product Ia:
  Yield: 70%
  Melting point: 157° C. to 159° C.
  IV ($cm^{-1}$): 3411 (O—H); 1736 (C=O ketone); 1682 (C=O starch); 1611 (C=O urea); 1175 (C—N)
  ESI-MS ([M+Na]$^+$ m/z, %): 475 (100)
  NMR-$^1$H (400 MHz; DMSO-d, δ, ppm); 1.79 (d, J=1.0 Hz, 3H, $CH_3$); 2.59)-2.70 (m, 2H, H-4"); 3.56-3.68 (m, 2H, $CH_2$—OH); 4.15-4.16 (m, 1H, H-2"); 4.98 (s, 2H, $CH_2$—NI); 5.27-5.33 (m, 1H, H-3"); 6.37 (t, J=6.5 Hz, 1H, H-5"); 7.14 (t, J=7.4 Hz, 1H, H-5); 7.20 (d, J=7.9 Hz, 1H, H-7); 7.54 (d, J=7.3 Hz, 1H, H-4); 7.64 (t, J=7.7 HZ, 1H, H-6); 7.78 (d, J=1.0 Hz, 1H, H-6'''); 8.33 (s, 1H, H-5'); 11.31 (s, 1H, NH)
  NMR-$^{13}$C (100 MHz; DMSO-d, δ, ppm): 12.2 ($CH_3$); 35.0 ($CH_2$—N1); 37.0 (C-4"); 59.3 (C-3"); 60.7 ($CH_2$—OH); 83.8 (C-2"); 84.4 (C-5"); 109.6 (C-5'''); 111.1 (C-7); 117.5 (C-3a); 123.2 (C-5'); 123.3 (C-5); 124.4 (C-4); 136.1 (C-6); 138.1 (C-6'''); 141.7 (C-4'); 150.1 (C-7a); 150.4 (C-2'''); 157.7 (C-2); 163.7 (C-4'''); 183.0 (C-3) HRMS (ESI$^+$)
  Theoretical value: 452.1444 ($C_{21}H_{20}N_{66}$)
  Amount obtained: 452.1449
  UPLC (%, nm): 95.2

Product Ib:
  Yield: 50%
  Melting point: 150° C. to 151° C.
  IV ($cm^1$): 3400 (O—H); 1747 (C=O ketone); 1694 (C=O starch); 1667 (C=O urea); 1176 (C—N)
  ESI-MS ([M+Na]$^+$, m/z, %): 489 (100)
  NMR-$^1$H (400 MHz; DMSO-d, δ, ppm); 1.79 (s, 3H, $CH_3$-5); 2.27 (s, 3H, $CH_3$-5'''); 2.60-2.71 (m, 2H, H-4"); 3.57-3.69 (m, 2H, $CH_2$—OH); 4.15-4.18 (m, 1H, H)-2"); 4.96 (s, 2H, $CH_2$—$N_1$); 5.29-5.34 (m, 1H, H-3"); 6.37 (t, J=6.6 Hz, 1H, H-5"); 7.08 (d, J=8.0 Hz, 1H, H-7); 7.39 (s, 1H, H-4); 7.46 (d, J=8.0 Hz, 1H, H-6); 7.78 (s, 1H, H-5$^1$); 8.32 (s, 1H, H-6'''); 11.31 (s, 1H, NH)
  NMR-$^{13}$C (100 MHz; DMSO-d, δ, ppm): 12.1 (C5'''-$CH_3$); 20.0 (C5-$CH_3$); 35.0 ($CH_2$—$N_1$); 37.0 (C-4"); 59.2 (C-3"); 60.7 ($CH_2$—OH); 83.8 (C-2"); 84.3 (C-5"); 109.5 (C-5'''); 111.0 (C-7); 117.5 (C-3a); 123.1 (C-5'); 124.6 (C-4); 132.7 (C-5); 136.1 (C-6); 138.4 (C-6'''); 141.8 (C-4'); 148.0 (C-7a); 150.3 (C-2'''); 157.8 (C)-2); 163.6 (C-4'''); 183.2 (C-3)
  HRMS (ESI$^+$)
  Theoretical value: 466.1601 ($C_{22}H_{22}N_{66}$)
  Amount obtained: 466.1602
  UPLC (%, nm): 96.4

Product Ic:
  Yield: 50%
  Melting point: 144° C. to 146° C. IV ($cm^{-1}$): 3367 (O—H); 1756 (C=O ketone); 1737 (C=O starch); 1702 (C=O urea); 1 178 (C—N)
  ESI-MS ([M+Na]$^+$, m/z, %): 509 (68)
  NMR-$^1$H (400 MHz; DMSO-d, δ, ppm): 1.82 (d, J=1.1 Hz, 3H, $CH_3$); 3.77-3.82 (m, 2H, H-4"); 3.87-3.92 (m, 2H, CHb-OH); 4.33-4.36 (m, 1H, H-2"); 4.54 (t, J=5.1 Hz, 1H, OH); 5.07 (s, 2H, $CH_2$—$N_1$); 5.46-5.51 (m. 1H, H-3"); 6.50 (t, J=6.6 Hz, 1H, H-5"); 7.33 (d, J=8.4 Hz, H-7); 7.56 (d, J=2.2 Hz, H-4); 7.68 (dd, Jo=8.4 Hz; Jm=2.2 Hz, 1H, H-6); 7.85 (d, J=1.1 Hz, 1H, H-6'''); 8.20 (s, 1H, H-5'); 9.98 (s, 1H, NH)
  NMR-$^{13}$C (100 MHz; DMSO-d, δ, ppm): 12.1 ($CH_3$); 35.0 ($CH_2$—N); 36.9 (C-4"); 59.2 (C-3"); 60.6 ($CH_2$—OH); 83.7 (C-2"); 84.3 (C-5"); 109.5 (C-5'''); 112.7 (C-7); 118.9

(C-3a); 123.2 (C-5'); 123.8 (C-4); 127.5 (C-5); 136.0 (C-6); 136.8 (C-6'''); 141.5 (C-4¹); 148.5 (C-7a); 150.3 (C-2'''); 157.4 (C-2); 163.6 (C-4'''); 181.8 (C-3) HRMS (ESI⁺)
Theoretical value: 486.1055 ($C_{21}H_{19}ClN_{66}$)
Amount obtained: 486.1046
UPLC (%, nm): 99.1
Product Id:
Yield: 40%
Melting point: 121° C. to 123° C.
IV (cm⁻¹): 3260 (N—H); 2979 (C—H sp³); 1715 (C=O ketone); 1688 (C=O starch); 1651 (C=O carbamate); 1374 (S=O); 1 172 (C—N)
ESI-MS ([M+Na]⁺, m/z, %): 739 (35)
NMR-¹H (400 MHz; CD₃COCD₃, δ, ppm): 0.90 (m, 8H, 14'-H; 15'-H); 1.95 (m, 11H, 23'-H; 24'-H); 3.00 (m, 5H, 12'-H; 13'-H; 16'-H); 3.76 (m, 8H, 17'-H; 20'-H; 21'-H; 2Z—H); 4.58 (s, 3H, CH₂—N; 18'-H); 7.19 (m, 8H, 4-H; 5-H; 7-H; 26'-H; 27'-H; 28'-H; 29'-H, 30'-H); 7.89 (s, 1H, 5'-H); 7.62 (m, 1H, 6-H); 8.02 (m, 2H, 7'-H; 8'-H)
NMR-¹³C (100 MHz; CD₃COCD₃, δ, ppm): 20.4 (C-14¹); 20.6 (C-15'); 24.4 (C— 13'); 30.8 (C-23'); 33.2 (C)-24'); 36.1 (CH₂—N); 53.2 (C-18¹); 57.4 (C-12'); 58.1 (C-16'); 67.9 (C-22'); 73.6 (C-20'); 74.2 (C-17'); 76.3 (C-21'); 110.9 (C-7); 119.4 (C-3a); 121.7 (C-8'; C-10'); 124.4 (C-4); 125.8 (C-28'); 127.2 (C-30'; C-26'); 129.2 (C-7'; C-11'); 130.4 (C-27'; C-29'); 130.7 (C-5); 140.2 (C-6); 140.9 (C-6'); 141.3 (C-9'); 144.7 (C-4'); 145.1 (C-7a; C-25'); 158.1 (C-2; C-19'); 184.1 (C-3) HRMS (ESI⁺)
Theoretical value: 716.2628 ($C_{36}H_{40}N_{68}S$)
Amount obtained: 716.2630
HPLC (%, nm): 88.3
Product Ie:
Yield: 55%
Melting point: 114° C. to 116° C.
IV (cm⁻¹): 3321 (N—H); 2962 (C—H sp³); 1727 (C=O ketone); 1689 (C=O starch); 1622 (C=O carbamate); 1340 (S=0); 1178 (C—N)
ESI-MS ([M+Na]⁺, m/z, %): 753 (100)
NMR-¹H (400 MHz; DMSO-d, δ, ppm): 0.82 (m, 7H, 14'-H; 15'-H); 1.74 (m, 2H, 24'-H); 1.89 (m, 3H, 13'-H; 23'-H); 2.27 (s, 3H, CH₃-5); 2.89 (m, 2H, 12'-H); 2.97 (m, 2H, 16'-H); 3.57 (m, 6H, 17'-H; 20'-H; 21'-H; 22'-H); 4.90 (m, 1H, 18'-H); 5.07 (s, 2H, CH₂—N); 7.15 (m, 8H, 7'-H; 26'-H; 27'-H; 28'-H; 29'-H; 30'-H); 7.44 (m, 2H); 8.02 (m, 4H, 7'-H; 8'-H; 10'-H; 11'-H)
NMR-¹³C (100 MHz; DMSO-d, δ, ppm): 19.7 (C-14'); 19.8 (C-15'); 20.0 (CH₃-5); 25.9 (C-13'); 32.1 (C-23'); 35.0 (CH₂—N); 35.2 (C-24'); 51.4 (C-16'); 55.6 C-12'; C-18'); 66.0 (C-22'); 71.5 (C-20'); 72.4 (C-21'); 110.9 (C-7); 117.6 (C-3a); 120.1 (C-8'; C-10'); 124.7 (C-4); 125.7 (C-28'); 127.9 (C-26'; C-30'); 128.9 (C-7'; C-11'); 129.0 (C-27'; C-29'); 132.8 (C-5); 138.3 (C-6); 138.9 (C-25¹); 139.2 (C-9'); 139.3 (C-6'); 143.3 (C"); 147.8 (C-7a); 155.5 (C-19'); 157.5 (C-2); 183.2 (C-3) HRMS (ESI⁺)
Theoretical value: 730.2785 ($C_{37}H_{42}N_{68}S$)
Amount obtained: 730.2789
UPLC (%, nm): 89.1
Product If:
Yield: 50%
Melting point: 110° C. to 112° C.
IV (cm¹): 2984 (C—H aliphatic); 1731 (C=O ketone); 1609 (C=O starch); 1239 (P=0); 1 176 (C—N)
ESI-MS ([M+Naf, m/z, %): 401 (100)
NMR-¹H (400 MHz; CD₃COCD₃, δ, ppm): 1.19 (t, J=7.0 Hz, 6H, CH₂—CH₃); 4.05 (m, 4H, 0-CH₂); 4.92 (d, J=13.0 Hz, 2H, CH₂—P); 5.06 (s, 2H, N1-CH₂); 7.16 (t, J=7.5 Hz, 1H, 5-H); 7.23 (d, J=8.0 Hz, 1H, 7-H); 7.56 (d, J=7.4 Hz, 1H, 4-H); 7.65 (t, J=7.8 Hz, 1H, 6-H); 8.06 (s, 1H, 5'-H)
NMR-¹³C (100 MHz; CD₃COCD₃, δ, ppm): 16.5 (d, J=5.6 Hz, CH₃); 35.9 (CH₂—N₁); 46.1 (d, J=152.1 Hz, CH₂—P); 63.5 (d, J=6.2 Hz, CH₂-0); 112.2 (C-7); 118.6 (C-3a); 124.3 (C-5'); 125.0 (C-5'); 125.1 (C-4); 138.9 (C-6); 142.9 (C-4'); 151.5 (C-7a); 158.5 (C-2); 184.1 (C-3)
NMR-³¹P (161 MHz; CD3C0CD3, δ, ppm): 16.1
HRMS (ESI⁺)
Theoretical value: 378.1093 ($C_{16}H_{19}N_{45}P$)
Amount obtained: 378.1095
UPLC (%, nm): 95.4
Product Ig:
Yield: 54%
IV (cm¹): 2979 (C—H aliphatic); 1732 (C=O ketone); 1621 (C=O starch); 1242 (P=0); 1183 (C—N)
ESI-MS ([M+Na]⁺, m/z, %): 415 (100)
NMR-¹H (400 MHz; CD₃COCD₃, δ, ppm): 1.19 (t, J=7.0 Hz, 6H, CH₂—CH₃), 2.31 (s, 3H, C5-CH₃); 4.05 (m, 4H, 0-CH₂); 4.92 (d, J=13.0 Hz, 2H, CH₂—P); 5.03 (s, 2H, CH₂—NI); 7.1 1 (d, J=8.0 Hz, 1H, 7-H); 7.38 (s, 1H, 4-H); 7.47 (d, J=8.0 Hz, 1H, 6-H); 8.04 (s, 1H, 5'-H) NMR-¹³C (100 MHz; CDCl3, δ, ppm): 16.5 (d, J=5.7 Hz, CH₂—CH₃); 20.4 (CH₃— C5); 35.9 (CH₂—N₁); 46.1 (d, J=152.2 Hz, CH₂—P); 63.5 (d, J=6.4 Hz, 0-CH₂); 112.0 (C-7); 118.7 (C-3a); 120.5 (C-5'); 125.4 (C-4); 134.1 (C-5); 139.3 (C-6); 143.0 (C-4'); 149.4 (C-7a); 158.6 (C-2); 184.3 (C-3)
NMR-³¹P (161 MHz; CD₃COCD₃, δ, ppm): 16.1
HRMS (ESI⁺)
Theoretical value: 392.1250 ($C_{17}H_{21}N_{45}P$)
Amount obtained: 392.1272
UPLC (%, nm): 99.5
Product Ih:
Yield: 30%
Melting point: 108° C. to 110° C.
IV (cm⁻¹): 2986 (C—H aliphatic); 1739 (C=O ketone); 1608 (C=O starch); 1243 (P=O); 1174 (C—N)
ESI-MS ([M+Na]⁺, m/z, %): 435 (100)
NMR-¹H (400 MHz; CD2Cl2, δ, ppm); 1.24 (t, J=7.0 Hz, 6H, CH₂—CH₃); 4.08 (m, 4H, O—CH₂); 4.71 (d, J=13.1 Hz, 2H, CH₂—P); 5.00 (s, 2H, CH₂—N₁); 7.23 (d, J=8.0 Hz, 1H, 7-H); 7.55 (d, J=8.0 Hz, 1H, 6-H); 7.57 (s, 1H, 4-H); 7.82 (s, 1H, 5'-H) NMR-¹³C (100 MHz; CD2Cl2, δ, ppm): 16.6 (d, J=5.7 Hz, CH₃); 36.0 (CH₂—N₁); 46.6 (d, J=154.0 Hz, CH₂—P); 64.0 (d, J=6.8 Hz, O—CH₂); 1 13.4 (C-7); 119.0 (C— 3a); 124.5 (C-5'); 125.4 (C-4); 130.1 (C-5); 138.2 (C-6); 149.3 (C-7a); 157.9 (C)-2); 182.8 (C-3)
NMR-³¹P (161 MHz; CD₃COCD₃, δ, ppm): 16.1
HRMS (ESI⁺)
Theoretical value: 412.0703 ($C_{16}H_{18}ClN_{45}P$)
Amount obtained: 412.0706
HPLC (%, nm): 98.0

Example 3—Synthesis of Formula II(A-f) Compounds

Before presenting the synthesis of the compounds de Formula II(a-f) it is necessary to describe the syntheses of the intermediaries VIII(a-c) that gave rise thereto.
Synthesis of Compounds VIII(a-c)
In a 100 mL bi-tube flask containing 10 mL of previously-dried THF, 40.8 mmol of cyclopropylacetylene (2 eq) and 40.8 mmol of n-BuLi (2 eq) (2.5M) were added. The reaction medium was initially kept under magnetic stirring at a temperature of −5° C. for 30 minutes. The reaction mixture was then cooled to a temperature of −78° C., and 20.4 mmol of the corresponding IV(a-c) isatins (1 eq) were added, with solubilized in 35 mL of anhydrous THF. The reaction was left under magnetic stirring overnight, and its termination was indicated by TLC, using hexane:ethyl acetate (1:1) elution system. After this period, a 1M citric acid solution was added until reaching pH 7. The organic phase was washed with water (3×10 mL), dried with anhydrous sodium sulphate and evaporated in order to obtain the corresponding brown solids.

Compound vIIIa:
Yield: 63%
Melting point: 197° C. to 199° C. (lit.: 198° C. to 199° C.) (BOECHAT, N.; KOVER, W. B.; BONGERTZ, V.; BASTOS, M. M.; ROMEIRO, N. C; AZEVEDO, M. L. G.; WOLLINGER, W. Design, synthesis and pharmacological evaluation of HIV-1 reverse transcriptase inhibition of new indolin-2-ones. Medicinal Chemistry, v. 3, No 6, page 533-542, 2007)
ESI-MS (IM+Na]+, m/z, %): 236 (100)

Compound vIIIb:
Yield: 37%
Melting point: 207° C. to 208° C. (lit.: 207° C. to 209° C.) (BOECHAT, N.; KOVER, W. B.; BONGERTZ, V.; BASTOS, M. M.; ROMEIRO, N. C; AZEVEDO, M. L. G.; WOLLINGER, W. Design, synthesis and pharmacological evaluation of HIV-1 reverse transcriptase inhibition of new indolin-2-ones. Medicine/Chemistry, v. 3, No 6, pages 533 to 542, 2007)
ESI-MS ([M+Na]+, m/z, %): 250 (100)

Compound vIIIc:
Yield: 30%
Melting point: 223° C. to 225° C. (lit.: 224° C. to 226° C.) (BOECHAT, N.; KOVER, W. B.; BONGERTZ, V.; BASTOS, M. M.; ROMEIRO, N. C; AZEVEDO, M. L. G.; WOLLINGER, W. Design, synthesis and pharmacological evaluation of HIV-1 reverse transcriptase inhibition of new indolin-2-ones. Medicinal Chemistry, v. 3, No 6, page 533-542, 2007)
ESI-MS ([M+Na]+, m/z, %): 246 (98)

Synthesis of compounds IX (a-c)

In a bi-tube flask, 4.6 mmol of corresponding VIII(a-c) intermediaries (1 eq) were added, with 8.7 mmol of potassium carbonate (1.9 eq), 1.4 mmol of sodium iodide (0.32 eq) and 0.1 mmol of 18-crown-6 (0.04 eq), propargyl bromide (1.63 eq) in 6 mL of dry DMF. The reaction was kept under magnetic stirring at room temperature for 22 hours, and its completion was indicated by TLC, using the hexane:ethyl acetate (1:1) elution system. The medium was then washed with DMF (20 mL) and vacuum filtered. The liquid was evaporated and an oil was obtained. To this oil, 20 mL of water was added and extracted with CHCl3(3×40 mL). The organic phase was dried with anhydrous sodium sulfate, filtered and the solvent was evaporated. the was purified through a chromatography column, using the chloroform: methanol elution system (9.5:0.5).

Compound IXa:
Yield: 97%
Melting point: 153° C. to 154° C.
IV (cm$^1$): 3331 (O—H); 2220 (C≡C), 1705 (C=O) CG/EM (70 eV, m/z, %): 212 (100); 222 (69); 146 (62); 251 (51); 156 (33) NMR-$^1$H (400 MHz; CD$_3$COCD$_3$) δ, ppm): 0.56-0.60 (m, 2H, H-11); 0.76-0.80 (m, 2H, H-11'); 1.25-1.32 (m, 1H, H-10); 2.81 (t, J=2.5 Hz, 1H, H-3'); 4.53 (d, J=2.5 Hz, 2H, H-1'); 5.85 (s, 1H, OH); 7.13 (m, 2H, H-5. H-7); 7.38 (td, Jo=7.7 Hz; Jm=1.2 Hz, 1H, H-6); 7.46 (dd, Jo=7.3 Hz; Jm=0.7 Hz, 1H, H-4)
NMR-$^{13}$C (100 MHz; CD$_3$COCD$_3$, δ, ppm)-0.003 (C-10); 8.7 (C-11, C-11'); 29.3 (C-1$^1$); 69.7 (C-8); 73.8 (C-3'); 73.9 (C-2'); 78.1 (C-3); 90.4 (C-9); 110.5 (C-7); 124.2 (C-5); 125.1 (C-4); 130.7 (C-6); 131.6 (C-3a); 142.1 (C-7a); 173.5 (C-2)

Compound IXb:
Yield: 70%
Melting point: 202° C. to 203° C.
IV (cm$^{-1}$): 3278 (OH); 2233 (C≡C); 1702 (C=O) CG/EM (70 eV, m/z, %): 226 (100); 265 (90); 160 (74); 236 (56); 180 (38) NMR-$^1$H (400 MHz; CD$_3$COCD$_3$, δ, ppm): 0.56-0.60 (m, 2H, H-11-0.76-0.80 (m, 2H, H-11'); 1.25-1.32 (m, 1H, H-10); 2.33 (s, 3H, CH$_3$); 2.80 (t, J=2.5 Hz, 1H, H-3'); 4.50 (d, J=2.5 Hz, 2H, H-1'); 5.78 (s, 1H, OH); 6.99 (d, J=7.9 Hz, 1H, H-7); 7.19 (d, J=7.9 Hz, 1H, H-6); 7.29 (s, 1H, H-4)
NMR-$^{13}$C (100 MHz; CDCl3, δ, ppm)-0.004 (C-10); 8.6 (C-11, C-11'); 21.0 (CH$_3$); 29.3 (C-1'); 69.8 (C-8); 73.7 (C-2'); 74.0 (C-3'); 78.2 (C-3); 90.2 (C-9); 110.2 (C-7); 125.8 (C-3a); 130.8 (C-6); 131.5 (C-5); 133.7 (C-4); 139.7 (C-7a); 173.5 (C-2)

Compound IXc:
Yield: 38%
IV (cm$^1$): 3331 (O—H); 3286 (C—H sp)-3000 (C—H sp$^3$); 2220 (C≡C); 1705 (C=O) CG/EM (70 eV, m/z, %): 246 (100); 180 (85); 285 (78); 256 (49); 166 (35) NMR-$^1$H (400 MHz; CD$_3$COCD$_3$16, ppm): 0.58-0.62 (m, 2H, H-11); 0.77-0.82 (m, 2H, H-11'); 1.27-1.34 (m, 1H, H-10); 2.33 (t, J=2.5 Hz, 1H, H-3'); 4.55 (d, J=2.5 Hz, 2H, H-1'); 6.05 (s, 1H, OH); 7.15 (d, J=8.3 Hz, 1H, H-7); 7.43 (dd, Jo=8.3 Hz; Jm=2.2 Hz, 1H, H-6); 7.46 (d, J=2.2 Hz, 1H, H-4)
NMR-$^{13}$C (100 MHz; CDCl316, ppm)-0.07 (C-10); 8.7 (C-11; C-11'); 29.3 (C-1'); 69.6 (C-8); 73.1 (C-2'); 74.1 (C-3'); 77.7 (C-3); 91.1 (C-9); 112.0 (C-7); 125.3 (C-4); 128.9 (C-5); 128.9 (C-3a); 130.5 (C-6); 140.9 (C-7a); 173.0 (C-2)

Synthesis of End-Products II(a-i)

Using a 50 mL mono-tube flask, were added 2.3 mmol of the corresponding acetylenes IX(a-c) (1.3 eq), 1.8 mmol of the X, XI or XII azides (1 eq), 0.1 mmol of sodium ascorbate (0.1 eq), 0.1 mmol of copper sulphate (0.06 eq) and 5 mL of a THF mixture with water (8:2). The reaction was kept under magnetic stirring at room temperature for 5 hours, with completion indicated by TLC through the hexane:ethyl acetate (3:7) elution system. At the end of the reaction, 30 mL of water were added, and the medium was extracted with CHCl$_3$ (3×50 mL). The organic phase was dried with anhydrous sodium sulphate, filtered and evaporated. The end-products were purified through a chromatography column, using a hexane:ethyl acetate (3:7) elution system.

Product IIa:
Yield: 64%
IV (cm$^1$): 3214 (O—H); 2233 (C≡C); 1682 (C=O starch); 1612 (C=O urea); 1170 (C—N) ESI-MS ([M-Hf, m/z, %): 517 (100)
NMR-$^1$H (400 MHz; CD$_3$COCD$_3$, δ, ppm): 0.55-0.59 (m, 2H, H-11); 0.76-0.79 (m, 2H, H-11'); 1.25-1.31 (m, 1H, H-10); 1.82 (d, J=1.1 Hz, 3H, CH$_3$); 2.70-2.82 (m, 2H, H-4"); 3.79-3.91 (m, 2H, CH$_2$—OH); 4.35-4.38 (m, 1H, H-2"); 4.97 (s, 2H, CH$_2$—N); 5.47-5.52 (m, 1H, H-3"); 5.71 (s, 1H, OH); 6.52 (t, J=6.6 Hz, 1H, H-5"); 7.08 (td, Jo=7.5 Hz; Jm=0.8 Hz, 1H, H-5); 7.15 (m, 1H, H-7); 7.31 (td, Jo=7.7 Hz; Jm=1.3 Hz, 1H, H-6); 7.42 (dd, Jo=7.4 Hz; Jm=0.8 Hz, 1H, H-4); 7.88 (d, J=1.1 Hz, 1H, H-6'"); 8.07 (d, J=2.0 Hz, 1H, H-5'); 10.04 (s, 1H, NH)
NMR-$^{13}$C (100 MHz; CD$_3$COCD$_3$, δ, ppm)-0.01 (G-10); 8.6 (C-11); 8.7 (C-11'); 12.6 (CH$_3$); 36.0 (CH$_2$—N); 38.7 (C-4"); 60.6 (C-3"); 62.2 (CH$_2$—OH); 69.7 (C-8); 74.0 (C-3); 85.9 (C-2"); 85.9 (C-5"); 90.2 (C-9); 110.7 (C-5'");

110.9 (C-7); 123.8 (C-5'); 123.9 (C-5); 125.0 (C-4); 130.6 (C-6); 131.6 (C-3a); 137.2 (C-6'''); 142.8 (C-4'); 143.4 (C-7a); 151.4 (C-2'''); 164.3 (C-4'''); 171.0 (C-2)

HRMS (ESI+)

Theoretical value: 518.1914 ($C_{26}H_{26}N_{66}$)

Amount obtained: 518.1910

HPLC (%, nm): 78.1

Product IIb:

Yield: 30%

IV (cm$^{-1}$): 3375 (O-H); 2232 (C≡C); 1666 (C=O starch); –1612 (C=O urea); –1 170 (C—N)

ESI-MS ([M-H]+, m/z, %): 531 (37)

NMR-$^1$H (400 MHz; $CD_3COCD_3$, δ, ppm): 0.56-0.60 (m, 2H, H-11); 0.75-0.80 (m, 2H, H-1 1'); 1.25-1.31 (m, 1H, H-10); 1.82 (d, J=1.1 Hz, 3H, $CH_3$-5'''); 2.30 (s, $CH_3$-5); 2.74-2.81 (m, 2H, H-4'¹); 3.88-3.91 (m, 2H, $CH_2$—OH); 4.33-4.37 (s, 1H, H-2"); 4.89 (s, 2H, $CH_2$—N); 5.47-5.51 (m, 1H, H-3"); 5.82 (s, 1H, OH); 6.52 (t, J=6.6 Hz, 1H, H-5"); 7.02 (d, J=7.9 Hz, 1H, H-7); 7.10-7.12 (m, 1H, H-6); 7.24 (s, 1H, H-4); 7.88 (d, J=1.2 Hz, 1H, H-6'''); 8.04 (d, J=2.4 Hz, 1H, H-5'); 10.05 (s, 1H, NH)

NMR-$^{13}$C (100 MHz; $CD_3COCD_3$, δ, ppm): 0.01 (C-10); 8.6 (C-1 1; C-11'); 12.6 (CH3-5); 21.0 ($CH_3$-5'''); 36.1 ($CH_2$—N); 38.7 (C-4"); 60.6 (C-3"); 62.1 ($CH_2$—OH); 69.8 (C-8); 74.2 (C-3); 85.9 (C-2"); 85.9 (C-5"); 90, 1 (C-9); 110.4 (C-5'''); 110.9 (C-7); 123.7 (C-5'); 125.7 (C-4); 130.8 (C-6); 131.6 (C-5); 133.4 (C-3a); 137.2 (C-6'''); 140.4 (C-4'); 143.5 (C-7a); 151.4 (C-2'''); 164.3 (C-4'''); 174.1 (C-2) HRMS (ESI+)

Theoretical value: 532.2070 ($C_{27}H_{28}N_{66}$)

Amount obtained: 532.2073

HPLC (%, nm): 82.5

Product IIc:

Yield: 40%

IV (cm$^{-1}$): 3500 (O-H)-2230 (C≡C); 1666 (C=O starch); 1620 (C=O urea); 1179 (C—N) ESI-MS ({M+Na}+, m/z, %): 575 (58)

NMR-$^1$H (400 MHz; DMSO-d, δ, ppm): 0.58-0.61 (m, 2H, H-11); 0.76-0.81 (m, 2H, H-11'); 1.32-1.39 (m, 1H, H-10); 1.80 (d, J=1.0 Hz, 3H, $CH_3$), 2.58-2.72 (m, 2H, H-4"); 3.58-3.69 (m, 2H, $CH_2$—OH); 4.17-4.19 (m, 1H, H-2"); 4.94 (s, 2H, $CH_2$—N); 5.33-5.37 (m, 1H, H-3"); 6.41 (t, J=6.6 Hz, 1H, H-5"); 7.17-7.19 (m, 1H, H-7); 7.39-7.41 (m, 2H, 4-H; H-6); 7.80 (d, J=1.0 Hz, 1H, H-6'''); 8.28 (s, 1H, H-5'); 11.34 (s, 1H, NH)

NMR-$^{13}$C (100 MHz; DMSO-d, δ, ppm): 0.8 (C-10); 8.0 (C-11; C-11'); 12.2 ($CH_3$); 35.0 ($CH_2$—N); 37.1 (C-4"); 59.3 (C-3"); 60.7 ($CH_2$—OH); 68.2 (C-8); 72.8 (C-3); 84.4 (C-2"); 84.4 (C-5"); 89.6 (C-9); 109.6 (C-5'''); 111.5 (C-7); 123.3 (C-5'); 123.3 (C-5); 123.9 (C-4); 129.5 (C-6); 132.5 (C-3a); 136.2 (C-6'''); 140.2 (C— 4'); 141.7 (C-7a); 150.4 (C-2'''); 163.7 (C-4'''); 172.4 (C-2)

HRMS (ESI+)

Theoretical value: 552.1524 ($C_{26}H_{25}ClN_{66}$)

Amount obtained: 552.1531

HPLC (%, nm): 98.6

Product IId:

Yield: 20%

ESI-MS ([M+Na]+, m/z, %): 467 (100)

Product IIe:

Yield: 20%

ESI-MS ([M]+, m/z, %): 481 (100)

IV (cm 1): 3269 (O—H); 2232 (C≡C); 1719 (C=O); 1228 (P=O)

NMR-1H (400 MHz; CD3COCD3, δ, ppm): 0.58 (m, 2H, 11-$H_2$); 0.77 (m, 1H, 12-$H_2$); 1.19 (t, J=7.0 Hz, 6H, CH2-CH3); 1.28 (m, 1H, 10-H); 2.29 (s, 3H, C5-CH3); 4.04 (m, 4H, CH2-O); 4.92 (d, J=13 Hz, 2H, CH2-P); 4.95 (s, 2H, CH2-$N_1$); 5.81 (s, 1H, OH); 6.98 (d, J=8 Hz, 1H, 6-H); 7.10 (d, J=8 Hz, 1H, 7-H); 7.24 (s, 1H, 4-H); 7.88 (s, 1H, 5'-H)

NMR-13C (100 MHz; CD3COCD3δ, ppm)-0.004 (C-10); 8.6 (C-1 1; C-12); 16.6 (d, J=5.5 Hz, CH3-CH2); 20.9 (C5-$C\_H_3$); 36.0 (CH2-$N_1$); 46.1 (d, J=151.8 Hz, CH2-P); 63.7 (d, J=6.3 Hz, O—CH2); 69.8 (C-8); 74.2 (C-3); 90.0 (C-9); 110.3 (C—7); 124.7 (C-5'); 125.6 (C-4); 130.7 (C-3a); 131.6 (C-6); 133.3 (C-4 1); 140.3 (C-5); 143.6 (C-7a); 174.1 (C-2)

NMR-31P (161 MHz; CD3COCD3, δ, ppm): 16.2

HRMS (ESI+)

Theoretical value: 458.1719 ($C_{22}H_{27}N_{45}P$)

Amount obtained: 458.1719

HPLC (%, nm): 100.0

Product IIf.

Yield: 30%

ESI-MS ([M+Na]m/z, %): 501 (100)

NMR-$^1$H (400 MHz; $CD_3COCD_3$, δ, ppm): 0.60 (m, 2H, 11-H); 0.79 (m, 2H, 12); 1.19 (t, J=7.0 Hz, 6H, $CH_3$); 1.29 (m, 1H, 10-H); 4.04 (m, 4H, $CH_2$—O); 4.92 (d, J=13 Hz, $CH_2$—P); 4.98 (s, 2H, $CH_2$—$N_1$); 6.06 (s, 1H, OH); 7.15 (d, J=8.3 Hz, 7-H); 7.34 (dd, J=2.2 Hz, 1H, 6-H); 7.40 (d, J=2.1 Hz, 1H, 4-H); 7.92 (s, 1H, 5'-H)

NMR-$^{13}$C (100 MHz; $CD_3COCD_3$, δ, ppm)-0.03 (C-10); 8.6 (C-11); 8.7 (C-12); 16.6 (d, J=5.7 Hz, $CH_3$); 36.1 ($CH_2$—$N_1$); 46.2 (d, J=151.8 Hz, $CH_2$—P); 63.7 (d, J=6.3 Hz, $CH_2$—O); 69.6 (C-8); 73.3 (C-3); 90.9 (C-9); 112.2 (C-7); 124.9 (C-5'); 125.1 (C-4); 128.6 (C-3a); 130.4 (C-6); 133.5 (C-5); 141.5 (C-4'); 143.2 (C-7a); 173.6 (C-2) NMR-$^{31}$P (161 MHz; $CD_3COCD_3$, δ, ppm): 16.2

HPLC (%, nm): 93.6

Example 4—Synthesis of End-Products III(A-i)

Before presenting the synthesis of the Formula III(a-i) compounds, it is necessary to describe the syntheses of the VI(a-c) and VII(a-c) intermediaries that gave rise thereto.

Synthesis of the VI(a-c) Compounds

Using a 50 mL mono-tube flask, 3.4 mmol of the corresponding IV(a-c) isatins (1 eq) was added, with 17 mmol of diethylaminosulfur trifluoride (DAST) (5 eq) and 30 mL of $CH_2Cl_2$. The reaction mixture was kept at room temperature under magnetic stirring for 4 hours and in a nitrogen atmosphere. The completion of the reaction was shown through TLC, using the hexane:ethyl acetate (7:3) elution system. The reaction was isolated through watching the reaction medium with water (3×30 mL). The organic phase was dried with anhydrous sodium sulfate, and the solvent was then evaporated, obtaining a brown solid as the end-product.

Compound vIa:

Yield: 77%

Melting point: 136° C. to 138° C. (lit. 137° C. to 139° C.) (BOECHAT, N. *Isatinas: mais umaprova de versatildade. Fluorodenitraçāo: uma alternativa*. 1996. 244f. PhD thesis in Organic Chemistry-Rio de Janeiro Federal University, Rio de Janeiro, 1996) CG/EM (70 eV, m/z, %): 141 (100); 114 (99); 169 (93); 75 (13); 126 (11)

Compound vIb:

Yield: 88%

Melting point: 157° C. to 159° C. (lit. 155° C. to 157° C.) (TORRES, J. C; GARDEN, S. J.; PINTO, A. C; DA SILVA, F. S. Q.; BOECHAT, N. A synthesis of 3-fluoroindoles and 3,3-difluoroindolins by reduction of 3,3-difluoro-2-oxindoles using a borane tetrahydrofuran complex. Tetrahedron, v. 55, pages 1881 to 1892, 1999) CG/EM (70 eV, m/z, %): 183 (100); 155 (76); 127 (35); 154 (23); 128 (14)

Compound vIc:
Yield: 68%
Melting point: 180° C. to 182° C. (lit. 183° C. to 185° C.) (BOECHAT, N. *Isatinas: mais umaprova de versatilidade. FluorodenitraØão: uma alternativa*. 1996. 244f. PhD thesis in Organic Chemistry-Rio de Janeiro Federal University, Rio de Janeiro, 1996) CG/EM (70 eV, m/z, %): 175 (100); 203 (83); 148 (60); 177 (31); 205 (27)

Synthesis of Compounds VII(a-c)

Using a 50 mL mono-tube flask, 2.9 mmol of the respective gem-difluorated VII(a-c) intermediaries (1 eq) were added, with 4.7 mmol of propargyl bromide (1.63 eq), 5.5 mmol of potassium carbonate (1.9 eq), 0.9 mmol of sodium iodide (0.32 eq) and 0.1 mmol of 18-crown-6 (0.04 eq) in 6 mL of distilled DMF. The reaction remained under magnetic stirring for 24 hours at room temperature, with its completion indicated through TLC (hexane: ethyl acetate 7:3). The reaction mixture was washed with 30 mL of DMF and vacuum filtered. The liquid was evaporated, obtaining a brown oil. The product was then washed, using chloroform ($CHCl_3$) (50 mL) and $H_2$ (3×25 mL). The organic phase was dried with anhydrous sodium sulfate and the solvent evaporated, forming the desired brown solid.

Compound vIIa:
Yield: 62%
Melting point: 76-78° C.
IV($cm^{-1}$): 3250 (C≡C—H); 2125 (C≡C); 1744 (C=O); 1368 (C—F)
CG/EM (70 eV, m/z, %): 168 (100); 207 (78); 179 (18); 178 (12); 126 (12) NMR-$^1$H (400 MHz; $CD_2Cl_2$, δ, ppm): 2.37 (t, J=2.5 Hz, 1H, H-3'); 4.49 (d, J=2.5 Hz, 2H, $H_2$-1'); 7.15 (d, J=7.6 Hz, 1H, H-7); 7.23 (t, J=7.6 Hz, 1H, H-5); 7.54-7.59 (m, 2H, H-4; H-6)
NMR-$^{13}$C (100 MHz; $CDCl_3$, δ, ppm): 29.5 (C-1'); 73.1 (C-3'); 75.4 (C-2'); 110.6 (C-7); 110.9 (t, J=247.9 Hz, C-3); 119.7 (t, J=23.0 Hz, C-3a); 124.2 (t, J=1.8 Hz, C-5); 124.6 (C-4), 133.7 (C-6); 142.2 (t, J=7.0 Hz, C-7a); 164.1 (t, J=30.5 Hz, C)-2)
NMR-$^{19}$F (376 MHz; $CD_2Cl_2$, δ, ppm): −111.9

Compound vIIb:
Yield: 77%
Melting point: 102° C. to 104° C.
IV ($cm^1$): 3248 (C≡C—H): 2126 (C≡C); 2919 ($CH_2$); 1747 (C=O); 1370 (C—F) CG/EM (70 eV, m/z, %): 221 (100); 182 (100); 192 (16); 222 (13); 178 (13) NMR-$^1$H (400 MHz; CDCb, δ, ppm): 2.29 (t, J=2.5 Hz, 1H, H-3'); 2.38 (s, 3H, $CH_3$); 4.47 (d, J=2.5 Hz, 2H, $H_2$-1'); 7.01 (d, J=8.0 Hz, 1H, H-7); 7.32 (d, J=8.0 Hz, 1H, H-6); 7.39 (m, 1H, H-4)
NMR-$^{13}$C (100 MHz; CDCb, δ, ppm): 20.9 ($CH_3$); 29.5 (C-1'); 73.5 (C-3'); 75.5 (C-2'); 110.3 (C-7); 110.9 (t, J=248.6 Hz, C-3); 119.9 (t, J=22.9 Hz, C-3a); 125.3 (C-4); 133.8 (C-5); 134.2 (t, J=1.9 Hz, C-6); 139.6 (t, J=7.0 Hz, C-7a); 164.3 (t, J=30.6 Hz, C-2)
NMR-$^{19}$F (376 MHz; $CDCl_3$, δ, ppm): −111.3

Compound vIIc:
Yield: 52%
Melting point: 87° C. to 89° C.
IV ($cm^{-1}$): 3259 (C—H sp); 2915 (C—H $sp^3$); 2126 (C≡C); 1754 (C=O); 1365 (C—F) CG/EM (70 eV, m/z, %): 241 (100); 202 (99); 243 (32); 204 (32); 178 (25) NMR-$^1$H (400 MHz; $CD_3COCD_3$, δ, ppm): 2.95 (t, J=2.5 Hz, 1H, 3'-H); 4.65 (d, J=2.5 Hz, 2H, 1'-$H_2$); 7.37 (m, 1H, 7-H); 7.71 (m, 1H, 6-H); 7.80 (q, J=1.8 Hz, 1H, 4-H)
NMR-$^{13}$C (100 MHz; CDCb, δ, ppm): 71.1 (C-1'); 74.8 (C-3'); 76.7 (C-2'); 111.3 (t, J=248.4 Hz, C-3); 111.3 (C-7); 121.9 (t, J=23.0 Hz, C-3a); 125.7 (C-4); 130.0 (t, J=2.1 Hz, C-5); 134.7 (t, J=2.1 Hz, C-6); 142.2 (t, J=7.0 Hz, C-7a); 164.3 (t, J=30.0 Hz, C-2) NMR<19>F (376 MHz; $CD_3COCD_3$, δ, ppm): −112.4

Synthesis of III(a-i) End-Products

Using a 50 mL mono-tube flask, 2.3 mmol of the corresponding VII(a-c) acetylenes (1.3 eq) were added, with 1.8 mmol of the X, XI or XII azides (1 eq), 0.1 mmol of sodium ascorbate (0.1 eq), 0.1 mmol of copper sulphate (0.06 eq) and 5 mL of a THF mixture with water (8:2). The reaction was kept under magnetic stirring at room temperature for 5 hours, with completion indicated by TLC through the hexane:ethyl acetate (3:7) elution system. At the end of the reaction, 30 mL of water were added, and the medium was extracted with $CHCl_3$ (3×50 mL). The organic phase was dried with anhydrous sodium sulphate, filtered and evaporated. The end-products were purified through a chromatography column, using a hexane:ethyl acetate (3:7) elution system.

Product IIIa:
Yield: 50%
Melting point: 127° C. to 130° C.
IV ($cm^1$): 3350 (O—H); 1756 (C=O starch); 1661 (C=O urea); 1372 (C—F); 1190 (C—N) ESI-MS ([M+Na]$^+$, m/z, %): 497 (66)
NMR-$^1$H (400 MHz; $CD_3COCD_3$16, ppm): 1.83 (d, J=1.1 Hz, 3H, $CH_3$); 2.75)-2.82 (m, 2H, H-4"); 3.79-3.92 (m, 2H, $CH_2$—OH); 4.35-4.37 (m, 1H, H-2"); 4.61 (s, 1H, OH), 5.06 (s, 2H, $CH_2$—$N_1$); 5.50-5.54 (m, 1H, H-3"); 6.52 (t, J=6.6 Hz, 1H, H-5"); 7.24 (t, J=7.6 Hz, 1H, H-5); 7.36 (d, J=8.0 Hz, 1H, H-7); 7.58 (td, Jo=7.8 Hz; Jm=1.2 Hz, 1H, H-6); 7.64 (dd, Jo=7.4 Hz; Jm=1.6 Hz, 1H, H-4); 7.88 (d, J=1.1 Hz, 1H, H-6'''); 8.23 (s, 1H, H-5'); 10.01 (s, 1H, NH)
NMR-$^{13}$C (100 MHz; $CD_3COCD_3$, δ, ppm): 12.5 ($CH_3$); 36.1 ($CH_2$—$N_1$); 38.6 (C— 4"); 60.7 (C-3"); 62.1 ($CH_2$—OH); 85.9 (C-2"); 86.0 (C-5"); 110.8 (C-5'''); 112.0 (t, J=246.5 Hz, C-3); 112.1 (C-7); 120.4 (t, J=22.9 Hz, C-3a); 124.0 (C-5'); 124.8 (C-5); 125.2 (C-4); 134.8 (C-6); 137.2 (C-6'''); 142.4 (C-4'); 144.2 (t, J-7.1 Hz, C-7a); 151.3 (C-2'''); 164.3 (C-4'''); 165.2 (t, J=30.1 Hz, C-2)
NMR-$^{19}$F (376 MHz; $CD_3COCD_3$, δ, ppm): −112.4
HRMS (ESI$^+$)
Theoretical value: 474.1463 ($C_{21}H_{20}F_2N_{65}$)
Amount obtained: 474.1468
UPLC (%, nm): 96.6

Product IIIb:
Yield: 40%
Melting point: 144° C. to 145° C.
IV ($cm^1$): 3367 (O—H); 1752 (C=O starch); 1686 (C=O urea); 1300 (C—F); 1 178 (C—N)
ESI-MS ([M+Naf, m/z, %): 487 (100)
NMR-$^1$H (400 MHz; $CD_3COCD_3$, δ, ppm): 1.82 (d, J=1.1 Hz, 3H, $CH_3$-5'''); 2.35 (s, 3H, $CH_3$-5); 2.75-2.91 (m, 2H, H-4"); 3.78-3.91 (m, 2H, $CH_2$—OH); 4.35-4.38 (m, 1H, H-2"); 4.54 (s, 1H, OH); 5.03 (s, 2H, $CH_2$—$N_1$); 5.48-5.53 (m, 1H, H-3"); 6.51 (t, J=6.6 Hz, 1H, H-5"); 7.23 (d, J=8.1 Hz, 1H, H-7); 7.38 (d, J=8.1 Hz, 1H, H-6); 7.46 (m, 1H, H-4); 7.87 (d, J=1.1 Hz, 1H, H-6'''); 8.20 (s, 1H, H-5'); 9.98 (s, 1H, NH)
NMR-$^{13}$C (100 MHz; $CD_3COCD_3$, δ, ppm): 12.5 (C5'''-$CH_3$); 20.7 (C5-$C_H_3$); 36.1 ($CH_2$—NI); 38.6 (C-4"); 60.7 (C-3"); 62.2 ($CH_2$—OH); 85.8 (C-2"); 86.0 (C-5"); 110.8 (C-5'''); 111.9 (C-7); 1 12.2 (t, J=246.6 Hz, C-3); 120.4 (t, J=22.6 Hz, C-3a); 123.9 (C-5'); 125.6 (C-4); 134.7 (C-5); 134.9 (C-6); 137.1 (C-6'''); 141.7 (t, J=7.0 Hz, C-7a); 142.5 (C-4'); 151.3 (C-2'''); 164.2 (C-4'''); 165.2 (t, J=30.0 Hz, C-2)

NMR-$^{19}$F (376 MHz; CD$_3$COCD$_3$, δ, ppm): −112.2
HRMS (IES$^+$)
Theoretical value: 488.1620 (C$_{22}$H$_{22}$F$_2$N$_{65}$)
Amount obtained: 488.1625
HPLC (%, nm): 100.0
Product IIIc:
  Yield: 50%
  Melting point: 242° C. to 243° C.
  IV (cm$^{-1}$): 3500 (OH); 1751 (C═O starch); 1715 (C═O urea); 1280 (C—F); 1179 (C—N)
  ESI-MS ([M+Naf, m/z, %): 531 (100)
  NMR-$^1$H (400 MHz; CD$_3$COCD$_3$, δ, ppm): 1.83 (d, J=1.2 Hz, 3H, CH$_3$); 2.76)-2.86 (m, 2H, H-4"); 3.79-3.92 (m, 2H, CH$_2$—OH); 4.35-4.37 (m, 1H, H-2"); 5.08 (s, 2H, CH$_2$—NI); 5.49-5.53 (m, 1H, H-3"); 6.51 (t, J=6.6 Hz, 1H, H-5"'); 7.38-7.41 (m, 1H, H-7); 7.61-7.64 (m, 1H, H-6); 7.74 (q, J=1.8 Hz, 1H, H-4); 7.87 (d, J=1.2 Hz, H-6"'); 8.24 (s, 1H, 5'-H)
  NMR-$^{13}$C (100 MHz; CD$_3$COCD$_3$, δ, ppm): 12.5 (CH$_3$); 36.2 (CH$_2$—N$_1$); 38.6 (C— 4"); 60.8 (C-3"); 62.1 (CH$_2$—OH); 85.8 (C-2"); 86.0 (C-5"); 110.9 (C-5"'); 111.4 (t, J=247.9 Hz, C-3); 113.8 (C-7); 121.9 (t, J=23.1 Hz, C-3a); 124.0 (C-5'); 125.5 (C-4); 129.6 (C-5); 134.6 (C-6); 137.1 (C-6"'); 142.1 (C-4'); 143.0 (t, J=6.8 Hz, C-7a); 151.3 (C-2"'); 164.2 (C-4"'); 164.8 (t, J=29.9 Hz, C-2)
  NMR-$^{19}$F (376 MHz; CD$_3$COCD$_3$, δ, ppm): −112.6
  HRMS (ESI)
  Theoretical value: 508.1074 (C$_{21}$H$_{19}$ClF$_2$N$_{65}$)
  Amount obtained: 508.1072
  UPLC (%, nm): 100
Product IIId:
  Yield: 20%
  Melting point: 103° C. to 104° C.
  IV (cm$^{-1}$): 2984 (C—H aliphatic); 1744 (C═O starch); 1089 (C—F); 1248 (P=O); 1194 (C—N)
  ESI-MS ([M+Na]$^+$, m/z, %): 423 (100)
  NMR-$^1$H (400 MHz; CD$_3$COCD$_3$, δ, ppm): 1.19 (t, J=7.0 Hz, 6H, CH$_3$); 4.06 (m, 4H, O—CH$_2$); 4.94 (d, J=13.0 Hz, 2H, CH$_2$—P); 5.07 (s, 2H, CH$_2$—N$_1$); 7.24 (t, J=7.6 Hz, 1H, 5-H); 7.33 (d, J=8.0 Hz, 1H, 7-H); 7.58 (t, J=8.0 Hz, 1H, 6-H); 7.64 (dd, J=8.0 Hz, 1H, 4-H); 8.06 (s, 1H, 5'-H)
  NMR-$^{13}$C (100 MHz; CD$_3$COCD$_3$, δ, ppm): 16.5 (d, J=5.7 Hz, CH$_3$); 36.0 (CH$_2$— N1); 46.1 (d, J=152.0 Hz, CH$_2$—P); 63.5 (d, J=6.3 Hz, 0-CH$_2$); 1 12.0 (t, J=246.5 Hz, C-3); 112.1 (C-7); 120.4 (t, J=23.0 Hz, C-3a); 124.8 (t, J=1.8 Hz, C-5'); 125.1 (C-5); 125.2 (C-4); 134.7 (C-6); 142.4 (C-4'); 144.1 (t, J=7.1 Hz, C-7a); 165.2 (t, J=30.1 Hz, C-2)
  NMR-$^{31}$P (161 MHz; CD$_3$COCD$_3$, δ, ppm): 16.1
  NMR-$^{19}$F (376 MHz; CD$_3$COCD$_3$, δ, ppm): −112.4
  HRMS (ESI$^+$)
  Theoretical value: 400.1112 (C$_{16}$H$_{19}$F$_2$N$_{44}$P)
  Amount obtained: 400.1112
  HPLC (%, nm): 100
Product IIIe:
  Yield: 20%
  Melting point: 116° C. to 118° C.
  IV (cm-1): 2980 (C—H aliphatic); 1734 (C═O); 1079 (C—F); 1250 (P=O); 1 187 (C— N)
  ESI-MS ([M-H]$^+$, m/z, %): 413 (100)
  NMR-$^1$H (400 MHz; CD$_3$COCD$_3$, δ, ppm): 1.19 (t, J=7 Hz, 6H, CH$_2$—CH$_3$); 2.34 (s, 3H, C5-CH$_3$); 4.05 (m, 4H, CH$_2$-0); 4.94 (d, J=13 Hz, 2H, CH$_2$—P); 5.04 (s, 2H, CH$_2$—NI); 7.20 (d, J=8.1 Hz, 1H, 7-H); 7.38 (d, J=8.1 Hz, 1H, 6-H); 7.46 (s, 1H, 4-H); 8.04 (s, 1H, 5'-H)
  NMR-$^{13}$C (100 MHz; CD$_3$COCD$_3$, δ, ppm): 16.5 (d, J=5.5 Hz, CH$_2$—CH3); 20.7 (C5-CH3); 36.0 (CH$_2$—N$_1$); 46.1 (d, J=151.8 Hz, CH$_2$—P); 63.6 (d, J=6.2 Hz, CH$_2$-0); 111.2 (t, J=246.6 Hz, C-3); 111.9 (C-7); 120.4 (t, J=22.6 Hz, C-3a); 125.0 (C-5'); 125.6 (C-4); 134.7 (t, J=1.8 Hz, C-5); 134.9 (C-6); 141.7 (t, J=7.2 Hz, C-7a); 142.5 (C-4'); 165.2 (t, J=30.0 Hz, C-2)
  NMR-$^{31}$P (161 MHz; CD$_3$COCD$_3$, δ, ppm): 16.1
  NMR-$^{19}$F (376 MHz; CD$_3$COCD$_3$) δ, ppm): −112.2
  HRMS (ESI$^+$)
  Theoretical value: 414.1268 (C$_{17}$H$_{21}$F$_2$N$_{44}$P)
  Amount obtained: 414.1263
  HPLC (%, nm): 99.8
Product IIIf:
  Yield: 16%
  Melting point: 119° C. to 120° C.
  IV (cm$^1$): 2984 (C—H aliphatic); 1749 (0=0); 1091 (C—F); 1239 (P═O); 1 187 (C— N)
  ESI-MS ([M+Na]$^+$, m/z, %): 457 (100)
  NMR-$^1$H (400 MHz; CD$_3$COCD$_3$, δ, ppm); 1.20 (t, J=7.0 Hz, 6H, CH$_2$—CH$_3$); 4.07 (m, 4H, O—CH$_2$); 4.94 (d, J=13.0 Hz, 2H, CH$_2$—P); 5.08 (s, 2H, CH$_2$—N$_1$); 7.37 (d, J=8.5 Hz, 1H, 7-H); 7.62 (d, J=8.5 Hz, 1H, 6-H); 7.74 (m, 1H, 4-H); 8.08 (s, 1H, 5'-H)
  NMR-$^{13}$C (100 MHz; CD$_3$COCD$_3$, δ, ppm): 16.5 (t, J=5.5 Hz, CH$_2$—C_H$_3$); 36.2 (CH$_2$—N$_1$); 46.2 (d, J=151.8 Hz, CH$_2$—P); 63.6 (d, J=6.1 Hz, O—CH$_2$); 11 1.4 (t, J=248.1 Hz, C-3); 113.8 (C-7); 122.0 (t, J=23.1 Hz, C-3a); 125.2 (C-5'); 125.5 (C— 4); 129.6 (t, J=1.8 Hz, C-5); 134.5 (C-6); 142.1 (C-4'); 143.0 (t, J=7.0 Hz, C-7a); 164.8 (t, J=29.8 Hz, C-2)
  NMR-$^{31}$P (161 MHz; CD$_3$COCD$_3$, δ, ppm): 16.1
  NMR-$^{19}$F (376 MHz; CD$_3$COCD$_3$, δ, ppm): −112.6
  HRMS (ESI$^+$)
  Theoretical value: 434.0722 (C$_{16}$H$_{18}$ClF$_2$N$_{44}$P)
  HPLC (%, nm): 100

Example 5—Antiretroviral Activity

All tests were conducted on three separate occasions. At least three independent experiments were performed and triplicates were run for each concentration. Through this method, the enzyme inhibition percentage was detected for each new molecule, which was then compared with the feasibility reduction percentage caused by TDF, AZT, efavirenz and nevirapine.

The results show that the new compounds are endowed with activities that are similar to or better than TDF and nevirapine. Furthermore, the tested molecules did not cause cytotoxic activity. The bio-assay results for the new I(a-i), II(a-i) and III(a-i) derivatives are described in Table 4. The main FIGURES present the mean results of three independent experiments. All the molecules presented enzyme inhibition activity with significantly low CI50 values. Particularly noteworthy were the Ie, Ig, IIIa, IIIc and IIIf molecules that were more active than the nevirapine and tenofovir benchmarks.

TABLE 4

BIO-ASSAYS OF NEW DERIVATIVES

| Substances | CI50 (µM) | CC$_{50}$ (µM) | IS |
|---|---|---|---|
| Ia | 2.5 | <100 | ND |
| Ib | 1.9 | <100 | ND |
| Ic | 1.9 | >100 | ND |
| Id | 1.5 | <100 | ND |
| Ie | 0.9 | <100 | ND |
| If | 1.3 | 2,317 | 1,782 |
| Ig | 0.7 | 2,058 | 2,940 |

TABLE 4-continued

BIO-ASSAYS OF NEW DERIVATIVES

| Substances | CI50 (µM) | CC$_{50}$ (µM) | IS |
|---|---|---|---|
| Ih | 1.2 | <100 | ND |
| IIa | 2.1 | >100 | ND |
| IIb | 3.3 | >100 | ND |
| IIc | 3.1 | >100 | ND |
| IId | 3.5 | >100 | ND |
| IIe | 1.8 | >100 | ND |
| IIf | 3.2 | >100 | ND |
| IIIa | 0.6 | 835 | 1392 |
| IIIb | 3.2 | <100 | ND |
| IIIc | 0.8 | 1054 | 1318 |
| IIId | 1.2 | 1496 | 1247 |
| IIIe | 2.2 | >100 | ND |
| IIIf | 0.9 | 1895 | 2106 |
| Va | U.A. | U.A. | ND |
| Vb | U.A. | U.A. | ND |
| Vc | U.A. | U.A. | ND |
| VIIa | U.A. | U.A. | ND |
| VIIb | U.A. | U.A. | NO |
| VIIc | U.A. | U.A. | NO |
| IXa | U.A. | U.A. | NO |
| IXb | U.A. | U.A. | ND |
| IXc | U.A. | U.A. | ND |
| Efavirenz | 0.01 | 88 | 8,800 |
| Nevirapine | 1.2 | 895 | 746 |
| Tenofovir | 1.2 | 680 | 567 |
| Zidovudine | 0.01 | 126 | 12,600 |

U.A. = Under analysis;
N.D. = not defined

The invention claimed is:

1. Compound derived from isatin, wherein the compound is a compound of Formulae I, II, or III, as shown below;

whereby in Formulae I, II, and III:

$R_1$ is selected from the group consisting of: H, $CH_3$, and Cl; and $R_2$ is selected from the group consisting of:

a radical of zidovudine, a radical of amprenavir, and an acyclic phosphonate chain, as shown below:

zidovudine amprenavir acrylic phosphonate chain

2. Compound of Formula 1 according to claim 1, wherein the compound is selected from the group consisting of:

1-((1-(2-(hydroxymethyl)-5-(5-methyl-2,4-dioxo-3,4-dihydropyrimidine-1(2H)-yl)tetrahydrofuran-3-yl)-1H-1,2,3-triazole-4-yl)methyl)indolin-2,3-dione;

1-((1-(2-(hydroxymethyl)-5-(5-methyl-2,4-dioxo-3,4-dihydropyrimidine-1 (2H)-yl)tetrahydrofuran-3-yl)-1H-1,2,3-triazole-4-yl)methyl)-5-methylindolin-2,3-dione;

5-chloro-1-((1-(2-(hydroxymethyl)-5-(5-methyl-2,4-dioxo-3,4-dihydropyrimidine-1(2H)-yl)tetrahydrofuran-3-yl)1H-1,2,3-triazole-4-yl)methyl)indoline-2,3-dione;

tetrahydrofuran-3-yl ((2S,3R)-4-(4-(4-((2,3-dioxoindolin-1-yl)methyl)-1H-1,2,3-triazole-1-yl)-N-isobutylphenylsulfonamide)-3-hydroxy-1-phenylbutan-2-yl) carbamate;

tetrahydrofuran-3-yl ((2S,3R)-3-hydroxy-4-(N-isobutyl-4-(4-((5-methyl-2,3-dioxoindolin-1-yl)methyl)-1H-1,2,3-triazole-1-yl)phenylsulfonamide)-1-phenylbutan-2-yl) carbamate;

tetrahydrofuran-3-yl ((2S,3R)-(4-(4-((5-chloro-2,3-dioxoindolin-1-yl)methyl)-1H-1,2,3-triazole-1-yl)-N-isobutylphenylsulfonamide)-3-hydroxy-1-phenylbutan-2-yl) carbamate;

diethyl ((4-((2,3-dioxoindolin-1-yl)methyl)-1H-1,2,3-triazole-1-yl)methyl) phosphonate;

diethyl ((4-((5-methyl-2,3-dioxoindolin-1-yl)methyl)-1H-1,2,3-triazole-1-yl)methyl) phosphonate; and diethyl ((4-((5-chloro-2,3-dioxoindolin-1-yl)methyl)-1H-1,2,3-triazole-1-yl)methyl) phosphonate.

3. Compound of Formula II according to claim 1, wherein the compound is selected from the group consisting, of:

1-(4-(4-((3-(cyclopropylethanol)-3-hydroxy-2-oxoindolin-1-yl)methyl)-1H-1,2,3-triazole-1-yl)-5-(hydroxymethyl)tetrahydrofuran-2-yl)-5-methylpyrimidine a-2,4(1H,3H)-dione;

1-(4-(4-((3-(cyclopropylethanol)-3-hydroxy-5-methyl-2-oxoindolin-1-yl)methyl)-1H-1,2,3-triazole-1-yl)-5-(hydroxymethyl)tetrahydrofuran-2-yl)-5-methylpyrimidine-2,4(1H,3H)-dione;

1-(4-(4-((5-chloro-3-(cyclopropylethanol)-3-hydroxy-2-oxoindolin-1-yl)methyl)-1H-1,2,3-triazole-l-yl)-5-(hydroxymethyl)tetrahydrofuran-2-yl)-5-methylpyrimidine-2,4(1H dione);

tetrahydrofuran-3-yl ((2S,3R)-4-(4-(4-((3-(cyclopropylethanol)-3-hydroxy-2-oxoindolin-1-yl)methyl)-1H-1,2,3-triazole-1-yl)-N-isobutylphenylsulfonamide)-3-hydroxy-1-phenylbutan)-2-yl)carbamate;

tetrahydrofuran-3-yl ((2S,3R)-4-(4-(4-((3-(cyclopropylethanol)-3-hydroxy-5-methyl-2-oxoindolin-1-yl)methyl)-1H-1,2,3-triazole-1-yl)-N-isobutylphenylsulfonamide)-3-hydroxy-1-phenylbutan-2-yl) carbamate;

tetrahydrofuran-3-yl ((2S,3R)-4-(4-(4-((5-chloro-3-(cyclopropylethanol)-3-hydroxy-2-oxoindolin-1-yl)methyl)-1H-1,2,3-triazole-1-yl)-N-isobutylphenylsulfonamide)-3-hydroxy-1-phenylbutan-2-yl) carbamate;

diethyl ((4-((3-(cyclopropylethanol)-3-hydroxy-2-oxoindolin-1-yl)methyl)-1H-1,2,3-triazole-l-yl)methyl) phosphonate;

diethyl ((4-((3-(dclopropylethanol)-3-hydroxy-5-methyl-2-oxoindolin-1-yl)methyl)-1H-1,2,3-triazole-1-yl)methyl) phosphonate; and diethyl ((4-((5-chloro-3-(cyclopropylethanol)-3-hydroxy-2-oxoindolin-1-yl)methyl)-1H-1,2,3-triazole-1-yl)methyl) phosphonate.

4. Compound of Formula III according to claim 1, wherein, the compound is selected from the group consisting of:

1-(4-(4-((3,3-difluor-2-oxoindolin-1-yl)methyl)-1H-1,2,3-triazole-1-yl)-5-(hydroxymethyl)tetrahydrofuran-2-yl)-5-methylpyrimidine-2,4(1H,3H)-dione;

1-(4-(4-((3,3-difluor-5-methyl-2-oxoindolin-1-yl)methyl)-1H-1,2,3-triazole-1-yl-5-(hydroxymethyl)tetrahydrofuran-2-yl)-5-methylpyrimidine-2,4(1H,3H)-dione;

1-(4-(4-((5-chloro-3,3-difluor-2-oxoindolin-1-yl)methyl)-1H-1,2,3-triazole-1-yl-5-(hydroxymethyl)tetrahydrofuran-2-yl)-5-methylpyrimidine-2,4(1H,3H)-dione;

tetrahydrofuran-3-yl ((2S,3R)-4-(4-(4-((3,3-difluor-2-oxoindolin-1-yl)methyl)-1H-1,2,3-triazole-1-yl)-N-isobutylphenylsulfonamide)-3-hydroxy-1-phenylbutan-2-yl) carbamate;

tetrahydrofuran-3-yl ((2S,3R)-4-(4-(4-((3,3-difluor-5-methyl-2-oxoindolin-1-yl)methyl)-1H-1,2,3-triazof-1-yl)-N-isobutylphenylsulfonamide)-3-hydroxy-1-phenylbutan-2-yl) carbamate;

tetrahydrofuran-3-yl ((2S,3R)-4-(4-(4-((5-chloro-3,3-difluor-2-oxoindolin-1-yl)methyl)-1H-1,2,3-triazole-1-yl)-N-isobutylphenylsulfonamide)-3-hydroxy-1-phenylbutan-2-yl) carbamate;

diethyl ((4-((3,3-difluor-2-oxoindolin-1-yl)methyl)-1H-1,2,3-triazole-1-yl)methyl) phosphonate;

diethyl ((4((3,3-difluor-5-methyl-2-oxoindolin-1-yl)methyl)-1H-1,2,3-triazole-1-yl)methyl) phosphonate; and diethyl ((4-((5-chloro-3,3-difluor-2-oxoindolin-1-yl)methyl)-1H-1,2,3-triazole-1-yl)methyl) phosphonate.

5. A pharmaceutical composition for the treatment of AIDS, wherein the pharmaceutical composition comprises a compound of Formulae I, II, or III compound as defined in claim 1.

6. A method of treatment for AIDS, wherein the method comprises the administration to a subject of a therapeutically effective quantity of at least one of the compounds of Formulae I, II, and III, as defined in claim 1.

7. A pharmaceutical composition for the treatment of an infection caused by HBV, wherein the pharmaceutical composition comprises a compound of Formulae I, II, or III compound as defined in claim 1.

8. A pharmaceutical composition for the treatment of a co-infection caused by HIV and HBV, wherein the pharmaceutical composition comprises a compound of Formulae I, II, or III as defined in claim 1.

9. A method for the treatment of an infection caused by HBV, wherein the method comprises administration to a host with an infection of a therapeutically effective quantity of at least one of the compounds of Formulae I, II, and III, as defined in claim 1.

10. A method for the treatment of a co-infection caused by HIV and HBV, wherein, the method comprises administration to a host with an infection of a therapeutically effective quantity of at least one of the compounds of Formulae I, II, and III, as defined in claim 1.

* * * * *